US007882135B2

(12) United States Patent
Brunner et al.

(10) Patent No.: US 7,882,135 B2
(45) Date of Patent: *Feb. 1, 2011

(54) METHOD FOR PREDICTING TREATMENT CLASSES USING BEHAVIOR INFORMATICS

(75) Inventors: Daniela Brunner, Bronx, NY (US);
Vijay Gondhalekar, New York, NY (US); Emer Leahy, Bedford, NY (US);
David LaRose, Pittsburgh, PA (US);
William P. Ross, Saranac Lake, NY (US)

(73) Assignee: Psychogenics, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,435

(22) Filed: Jul. 31, 2009

(65) Prior Publication Data

US 2010/0106743 A1 Apr. 29, 2010

Related U.S. Application Data

(63) Continuation of application No. 11/741,312, filed on Apr. 27, 2007, now Pat. No. 7,580,798, which is a continuation of application No. 10/147,334, filed on May 15, 2002, now Pat. No. 7,269,516.

(60) Provisional application No. 60/291,039, filed on May 15, 2001, provisional application No. 60/326,271, filed on Oct. 1, 2001.

(51) Int. Cl.
*G06F 17/30* (2006.01)
(52) U.S. Cl. .................. 707/791; 707/802; 382/110; 382/128
(58) Field of Classification Search .............. 707/802, 707/791, 999.1; 382/110, 128; 702/19; 380/713; 713/176; 714/45
See application file for complete search history.

(56) References Cited

U.S. PATENT DOCUMENTS 3,100,473 A 8/1963 Kissel (Continued)

FOREIGN PATENT DOCUMENTS

EP 0 363 755 4/1990

(Continued)

OTHER PUBLICATIONS

Abe, et al., "Scene Retrieval Method Using Temporal Condition Changes", Systems and Computers in Japan, 24:7, pp. 92-101 (1993).

(Continued)

*Primary Examiner*—Cheryl Lewis
(74) *Attorney, Agent, or Firm*—Kenneth H. Sonnenfeld; King & Spalding LLP

(57) ABSTRACT

A system and method used to assess animal behavior includes a module having sensors that collects a variety of physical and biological data from a test subject. Interpretation of the data is provided to assess the test subject's behavior, neurology, biochemistry and physiology. The module is useful in observing the effects of a drug on the test animal and providing information on the drug's signature. Another advantage is the module's portability that allows it to be used in standard laboratory cages. This portability allows the animal to be tested in its own habitat, that can reduce any erroneous data due to stressing the animal when removed to a test cage. Additionally, the module's design allows for parallel data collection and interpretation from several laboratory animals undergoing different experiments. Multi-dimensional modeling of the test subject based the system's interpretation of the data allows pattern recognition of the drug signature, and predictive drug analysis.

3 Claims, 16 Drawing Sheets

U.S. PATENT DOCUMENTS

| | | | |
|---|---|---|---|
| 3,656,456 A | 4/1972 | Stigmark et al. | |
| 3,803,571 A | 4/1974 | Luz | |
| 3,955,534 A | 5/1976 | Boudrot et al. | |
| 3,974,798 A | 8/1976 | Meetze, Jr. | |
| 4,337,726 A | 7/1982 | Czekajewski et al. | |
| 4,448,150 A | 5/1984 | Catsimpoolas | |
| 4,574,734 A | 3/1986 | Mandalaywala et al. | |
| 4,631,676 A | 12/1986 | Pugh | |
| 4,693,255 A | 9/1987 | Beall | |
| 4,813,436 A | 3/1989 | Au | |
| 5,080,109 A | 1/1992 | Arme, Jr. | |
| 5,088,446 A | 2/1992 | Campiotti | |
| 5,148,477 A | 9/1992 | Neely et al. | |
| 5,214,711 A | 5/1993 | Neely et al. | |
| 5,243,418 A | 9/1993 | Kuno et al. | |
| 5,339,166 A | 8/1994 | LeBrat et al. | |
| 5,428,774 A | 6/1995 | Takahashi et al. | |
| 5,493,344 A | 2/1996 | Yu | |
| 5,550,965 A | 8/1996 | Gabbe et al. | |
| 5,666,157 A | 9/1997 | Aviv | |
| 5,710,833 A | 1/1998 | Moghaddam et al. | |
| 5,721,692 A | 2/1998 | Nagaya et al. | |
| 5,724,983 A | 3/1998 | Selker et al. | |
| 5,734,737 A | 3/1998 | Chang et al. | |
| 5,748,775 A | 5/1998 | Tsuchikawa et al. | |
| 5,774,591 A | 6/1998 | Black et al. | |
| 5,794,569 A | 8/1998 | Titus et al. | |
| 5,798,798 A | 8/1998 | Rector et al. | |
| 5,802,220 A | 9/1998 | Black et al. | |
| 5,850,352 A | 12/1998 | Moezzi et al. | |
| 5,864,862 A | 1/1999 | Kriens et al. | |
| 5,870,138 A | 2/1999 | Smith et al. | |
| 5,875,305 A | 2/1999 | Winter et al. | |
| 5,886,788 A | 3/1999 | Kobayashi | |
| 5,915,332 A | 6/1999 | Young et al. | |
| 5,969,755 A | 10/1999 | Courtney | |
| 6,023,497 A | 2/2000 | Takahashi et al. | |
| 6,061,088 A | 5/2000 | Khosravi et al. | |
| 6,062,224 A | 5/2000 | Kissinger et al. | |
| 6,072,903 A | 6/2000 | Maki et al. | |
| 6,081,607 A | 6/2000 | Mori et al. | |
| 6,128,396 A | 10/2000 | Hasegawa et al. | |
| 6,140,316 A | 10/2000 | Berliner et al. | |
| 6,173,290 B1 * | 1/2001 | Goldberg | 707/687 |
| 6,212,510 B1 | 4/2001 | Brand | |
| 6,231,527 B1 | 5/2001 | Sol | |
| 6,234,109 B1 | 5/2001 | Andersson et al. | |
| 6,263,088 B1 | 7/2001 | Crabtree et al. | |
| 6,353,831 B1 | 3/2002 | Gustman | |
| 6,432,938 B1 | 8/2002 | Jennings-White et al. | |
| 6,678,413 B1 | 1/2004 | Liang et al. | |
| 6,899,686 B2 | 5/2005 | Hampton et al. | |
| 7,068,842 B2 | 6/2006 | Liang et al. | |
| 7,269,516 B2 * | 9/2007 | Brunner et al. | 702/19 |
| 7,580,798 B2 * | 8/2009 | Brunner et al. | 702/19 |
| 2002/0177110 A1 | 11/2002 | Kurokawa | |
| 2004/0141635 A1 | 7/2004 | Liang et al. | |
| 2004/0141636 A1 | 7/2004 | Liang et al. | |
| 2006/0110049 A1 | 5/2006 | Liang et al. | |
| 2009/0285452 A1 | 11/2009 | Liang et al. | |
| 2009/0296992 A1 | 12/2009 | Liang et al. | |

FOREIGN PATENT DOCUMENTS

| | | |
|---|---|---|
| EP | 0 579 319 | 1/1994 |
| EP | 0 624 313 | 11/1994 |
| EP | 0 743 043 | 11/1996 |
| EP | 0 933 726 A2 | 8/1999 |
| JP | 63-133061 | 6/1988 |
| JP | 63-233318 | 9/1988 |
| JP | 8032959 | 2/1996 |
| JP | 08063603 | 3/1996 |
| JP | 08240830 | 9/1996 |
| JP | 09073541 | 3/1997 |
| JP | 9237348 | 9/1997 |
| JP | 10019658 | 1/1998 |
| JP | 10258044 | 9/1998 |
| JP | 11052215 | 2/1999 |
| JP | 11063927 | 3/1999 |
| JP | 11094599 | 4/1999 |
| JP | 11235328 | 8/1999 |
| JP | 11-259643 | 9/1999 |
| JP | 11-296651 | 10/1999 |
| JP | 11316820 | 11/1999 |
| JP | 2000000216 | 1/2000 |
| JP | 2000215319 | 8/2000 |
| JP | 3270005 | 4/2002 |
| SU | 1357010 | 12/1987 |
| WO | WO 00/39336 | 7/2000 |
| WO | WO 00/65523 | 11/2000 |
| WO | WO 01/12171 | 2/2001 |
| WO | WO 01/12184 A1 | 2/2001 |
| WO | WO 01/58351 | 8/2001 |
| WO | WO 02/43352 | 5/2002 |
| WO | WO 02/44992 | 6/2002 |
| WO | WO 02/092101 | 11/2002 |

OTHER PUBLICATIONS

Babu, K.S., et al., Spike Burst Analysis: A Tool for Analyzing Spontaneous Prehension Behaviors Recorded with Digital Video. Society for Neuroscience's 30$^{th}$ Annual Meeting (Nov. 4-9, 2000), p. 1.

Balch, T., et al. Automatically Tracking and Analyzing the Behavior of Live Insect Colonies. School of Computer Science, Carnegie Mellon University, Pittsburgh, PA (2001), pp. 1-9.

Barber, D.L., et al. An Automatic Apparatus for Recording Rotational Behaviour in Rats with Brain Lesions. *Physiology & Behavior* 11, 117-120 (1973).

Battaglia, D., et al.; (1995). The role of physical cues in the regulation of host recognition and acceptance behavior of Aphidius ervi Haliday (Hymenoptera: Braconidae). Journal of Insect Behavior, 8, 739-750.

Baumans, V., et al. Development of a Balance System for Analysis of Rodent Behavior. *Measuring Behavior '96* retrieved from http://www.noldus.com/events/mb96/abstract/baumans.htm on Jan. 14, 2002, p. 1.

Baumberg, A. M., et al., "Learning Flexible Models from Image Sequences", University of Leeds, School of Computer Studies Research Report Series, Report 93.36, Oct. 1993, pp. 1-13.

Baumberg, Adam, et al., "Learning Flexible Models from Image Sequences", Lecture Notes in Computer Science, vol. 800, Jan-Olof Eklundh (Ed.), Computer Vision—ECCV 1994, pp. 299-308.

Beer, R., "A Simple Method for Recording and Analyzing Spatial Behaviour", Measuring Behavior '96, International Workshop on Methods and Techniques in Behavioral Research, 1996.

Bengtsson, G., et al. Irregular walks and loops with handedness in small-scale movement of Onychirus armatus (Collembola). *Dept. of Ecology and Centre for Mathematical Studies*, Lund University, Sweden retrieved from http://www.math.ku.dk/~magnusw/onychart2abs.txt on Jan. 10, 2002, p. 1.

Bevilacqua, et al., "Robust Denoising and Moving Shadows Detection in Traffic Scenes" (2001).

Bigelow, J.A., et al., Feeding and Drinking Patterns in Young Pigs. *Physiology & Behavior* 43, 99-109 (1988).

Bobick, Aaron, et al., "Real-time Recognition of Activity Using Temporal Templates", Third IEEE Workshop on Applications of Computer Vision WACV '96, pp. 39-42 (1996).

Brand, M., "Learning concise models of human activity from ambient video . . . " MERL, Mitsubishi Electric Research Laboratory (Nov. 1997).

Brand, M., et al., Discovery and Segmentation of Activities in Video. *IEEE Transactions on Pattern Analysis and Machine Intelligence* 22, 844-851 (Aug. 2000).

Brandl, N., Measuring Pig Travel by Image Analysis. *Semi-automatic pc program for tracking animal* retrieved from http://nabilnabil.homestead.com/files/movtrack.htm on Jan. 10, 2002, pp. 1-5.

Brann, M,R., et al., A Device for the Automated Monitoring of Stereotypic Behavior. *Prog. Neuro-Psychopharmacol & Biol. Psychiat.* 6, 351-354 (1982).

Bressers, W.M.A., et al., 1995. Time structure of self grooming in the rat: self-facilitation and effects of hypothalamic stimulation and neuropeptides. Behavioural Neurosciences, 109, 955-964.

Carson, Chad, et al., "Blobworld: A system for region-based image indexing and retrieval" (1999). Abstract Retrieved from http://elib.cs.berkeley.edu/carson/papers/visual99.html.

Cavallaro, et al., "Image Analysis for Advanced Video Surveillance" (2000).

Cohen, Isaac, et al., "Detecting and Tracking Moving Objects for Video Surveillance", IEEE Proc. Computer Vision and Pattern Recognition, pp. 1-7, 1999.

Collins, R.T., et al. A System for Video Surveillance and Monitoring. The Robotics Institute, Carnegie Mellon University, Pittsburgh PA 1-53 (2000).

Connor, et al., "Infrared video viewing," Science, 1999 (1978).

Cools, A.R., et al., Image-Analyzing Systems for the Study of Rodent Behaviour: Spatial and Postural Transitions of Stable Configurations in Time. *Measuring Behavior '96* retrieved from http://www.noldus.com/events/mb96/abstract/cools.htm on Jan. 14, 2002, pp. 1-2.

Cools, A.R., et al., Image-analyzing systems for the study of spatial and postural transitions in rats. *Measuring Behavior 1998* retrieved from http://www.noldus.com/events/mb98/abstracts/cools.htm on Jan. 14, 2002, p. 1.

Cools, et al., "Image-analyzing systems for the study of rodent behavior: spatial and postural . . . " Paper presented at Measuring Behavior '96, International Workshop (Oct. 1996).

Crnic, et al., "Animal Models of Mental Retardation: An Overview", Mental Retardation and Developmental Disabilities, 2:185-187 (1996).

Crnic, L.S., et al., Automated Analysis of Digitized Videotapes of Mouse Home-Cage Behavior. Society for Neuroscience's 30$^{th}$ Annual Meeting (Nov. 4-9, 2000), p. 1.

Davis, James W., et al., "The Representation and Recognition of Human Movement Using Temporal Templates", IEEE Computer Society Conference on Computer Vision and Pattern Recognition, pp. 928-934 (1997).

Day, et al., "Object-Oriented Conceptual Modeling of Video Data", IEEE pp. 401-408 (1995).

De Vries, Han, et al., "Matman: A Program for the Analysis of Sociometric Matrices and Behavioural Transition Matrices", Behaviour, vol. 125, pp. 157-175 (1993).

Debowy, D.J., et al., Spike Burst Analysis: A Tool for Analyzing Trained Prehension Behaviors Recorded with Digital Video. Society for Neuroscience's 30$^{th}$ Annual Meeting (Nov. 4-9, 2000), p. 1.

Duncan, "Using Theme to Analyze Interaction Structure and Strategy", Measuring Behavior, www.noldus.com/events/mb2002/programlabstracts/duncan.html (2002).

Everingham, M., et al., "Supervised segmentation and tracking of nonrigid objects using a 'Mixture of Histograms' Model," 2001, IEEE International Conference on Image Processing, Thessaloniki, Greece.

Fergusson, I.K., Tracking sharks by videocamera—Crittercam: the video parasite. *Ichthyology at FL Museum of Nat. Hist.* Retrieved from http://www.flmnh.ufl.edu/fish/Organizations/SSG/7Newsletter/shark7news11.htm on Jan. 10, 2002, p. 1.

Golani, I., Research in the interface between behaviour, computation, statistics and genetics. *Laboratory of Animal Behavior*, Tel Aviv University retrieved from http://www.tau.ac.il/~ilan99 on Jan. 10, 2002, pp. 1-3.

Golani, Ilan, et al., "Early Ontogeny of Face Grooming in Mice", Development Psychobiology, 18(6):529-544 (1985).

Haccou, P., et al., 1983. Analysis of time-in homogeneity in Markov chains applied to mother-infant interactions of rhesus monkeys. Animal Behaviour, 31, 927-945.

Haccou, P., et al., 1986. On the analysis of time—in homogeneity in Markov chains: a refined test for abrupt behavioural changes. Animal Behaviour, 34, 302-303.

Harville, "A Framework for High-Level Feedback to Adaptive, Per-Pixel, Mixture of Gaussian Background Models", ECCV (2002).

Hendrie, C.A., et al., "A Microcomputer Technique for the Detailed Analysis of Animal Behaviour", Physiology & Behavior, vol. 30, pp. 233-235, Pergamon Press, 1983.

Hereen, et al., "Classifying postures of freely moving rodents with the help of Fourier descriptors and a neural network," Behav. Res. Meth. Instr. Comp., 32, 56-62 (2000).

Hopper, D. L., et al., "Reproducibility of Time Structure in Motor Activity of Rats Under Nocturnal Conditions", Pharmacology Biochemistry and Behavior, vol. 42, pp. 245-250,1992.

Hora, K.H., et al., 1999, Oviposition in Yponomeuta cagnagellus: the importance of contact cues for host plant acceptance. Physiological Entomology, 24, 109-120.

Horprasert, et al., "A Statistical Approach for Real-Time Robust Background Subtraction and Shadow Detection" (1999).

Hoy, J.B., Dynamic Animal Movement Analyzer: A Macintosh-Based Video Animal Tracker. *Dept. Entomology & Nematology*, University of Florida, Gainesville retrieved from http://www.afpmb.org/pubs/presen10.htm on Jan. 10, 2002.

Huang, J., et al., "Joint Video Scene Segmentation and Classification Based on Hidden Markov Model," 2000, IEEE International Conference on Multimedia and Expo, New York, NY, pp. 1551-1554.

Intille, Stephen S., et al., "Real-Time Closed-World Tracking", Proceedings of the IEEE Computer Society Conference on Computer Vision and Pattern Recognition, pp. 697-703 (1997).

Isaacs, R., et al., (1999). Host plant evaluation behaviour of Bemisia Tabaci and its modification by external or internal uptake of imidacloprid. Physiological Entomology, 24, 101-108.

Jenkins, et al., "Deriving Action and Behavior Primitives from Human Motion Data", IEEE,RSJ Int'l Conf. on Intell. Robots and Systems, pp. 2551-2556 (2002).

Jiang, Haitao, "A Video Database System for Studying Animal Behavior", Multimedia Storage and Archiving Systems, Nov. 18-19, 1996; Boston, Massachusetts, SPIE—The International Society For Optical Engineering, vol. 2916, pp. 162-173.

Jonsson, G.K., "Detecting patterns in complex behavioural processes with The Observer and Theme", Poster presented at Measuring Behavior '98, 2$^{nd}$ International Conference on Methods and Techniques in Behavioral Research (1998). Retrieved from http://www.hi.is/~msm/posterbeggi/index.html.

Kamijo, S., et al., Occlusion Robust Vehicle Tracking for Behavior Analysis utilizing Spatio-Temporal Markow Random Field Model. *IEEE Intelligent Transportation Systems.* Conference Proc. Dearborn, MI 340-345 (2000).

Kernan, Jr., W.J., et al., "Computer Technology, Pattern Recognition of behavioral events in nonhuman primate", Behavior Research Methods & Instrumentation, vol. 12 (5), pp. 524-534, 1980.

Kernan, Jr., W.J., et al., Pattern Recognition of Rat Behavior. *Pharmacol. Biochem. Behav.* 27, 559-564 (1987).

Kernan, Jr., W.J., et al., "Analysis of the Time Distribution And Time Sequence of Behavioral Acts", Intern J. Neuroscience, 1988, vol. 43, pp. 35-51.

Kernan, Jr., W.J., et al., "Time Structure Analysis of Behavioral Acts Using a Computer Pattern Recognition System", Pharmacology Biochemistry and Behavior, vol. 34, pp. 863-869, 1989.

Kobla, Vikrant, et al., "Archiving, indexing, and retrieval of video in the compressed domain", Multimedia Storage and Archiving Systems, Nov. 18-19, 1996, SPIE—The International Society For Optical Engineering, vol. 2916, pp. 78-89.

Kobla, Vikrant, et al., "Compressed Domain Video Segmentation", Center for Automation Reseach, University of Maryland, Sep. 1996, pp. 1-25.

Kobla, Vikrant, et al., "Feature Normalization for Video Indexing and Retrieval", Center for Automation Research and Dept. of Computer Science, Inst. for Systems Research, University of Maryland, Nov. 1996, pp. 1-38.

Kojima, A, et al., Generating Natural Language Description of Human Behavior from Video Images. *Proc. 15$^{th}$ International Conference on Pattern Recognition*, IEEE Computer Society 4,728-731 (2000).

Krill, P., Attention shoppers: You may be studied. (Jan. 11, 2002). *InfoWorld* retrieved http://staging.infoworld.com/artic...ate=/storypages/printfriendly.html on Jan. 14, 2002, pp. 1-2.

Kuhl, et al., "Elliptic fourier features of a closed contour," Comp. Graphics & Image Proc., 18, 236-258 (1982).

Liang, "Digital video analysis system for home cage behavior," CRISP NIH database, Grant No. IR43MH058964-01, Project Start: Jul. 1, 1999 (date posted to public database).

Liang, "Digital video analysis system for home cage behavior," CRISP NIH database, Grant No. 2R44MH058964-02, Project Start: Jul. 1, 1999 (date posted to public database).

Liang, "High Throughput Phenotyping: Drug Effects on Homecage mo", CRISP NIH database, Project Start: Sep. 30, 2001 (date posted to public database).

Liang, et al., "A Practical Video Indexing and Retrieval System", SPIE, vol. 3240 (1998).

Liang, et al., "A Ground Target Detection System for Digital Video Database" SPIE, vol. 3387 (1998).

Lyon, Melvin, et al, "The importance of temporal structure in analyzing schizophrenic behavior: some theoretical and diagnostic implications", Schizophrenia Research, vol. 13, pp. 45-56 (1994).

MacIver, M.A., et al., Body modeling and model-based tracking for neuroethology. *J. Neurosci. Methods* 95,133-143 (2000).

MacIver, M.A., et al., Prey-Capture Behavior in Gymnotid Electric Fish: Motion Analysis and Effects of Water Conductivity. *J. Exp. Biol.* 204, 543-557 (2001).

Magnusson, "Discovering Hidden Time Patterns in Behavior: T-Patterns and Their Detection", Beh. Res. Methods, Instr. & Comp., 32:1, 93-110 (2000).

Magnusson, M.S., "Real-time pattern detection versus standard sequential and time series analysis", Measuring Behavior '98, $2^{nd}$ international Conference on Methods and Techniques in Behavioral Research (1998): Retrieved from http://www.noldus.com/events/mb98/abstracts/Magiiusson.htm.

Magnusson, M.S., "T-Patterns, Theme and the Observer", Measuring Behavior '96, International Workshop on Methods and Techniques in Behavioral Research (1996). Retrieved from http://www.noldus.com/events/mb96/abstract/magnusso.htm.

Magnusson, Magnus S., "Hidden Real-Time Patterns in Intra- and Inter-Individual Behavior: Description and Detection", European Journal of Psychological Assessment, vol. 12, pp. 112-123 (1996).

Martin, B.R., et al., Quantitation of Rodent Catalepsy by a Computer-Imaging Technique. *Pharmacology Biochemistry and Behavior* 43, 381-386 (1992).

Medioni, Gérard, et al., "Event Detection and Analysis from Video Streams", IEEE Transactions on Pattern Analysis and Machine Intelligence, vol. 23, 873-889 (Aug. 2001).

Morrow-Tesch, J., et al., A Video Data Base System for Studying Animal Behavior. *J. Anim. Sci.* 76,2605-2608 (1998).

Mullenix, P.J., et al., "Extension Of The Analysis Of The Time Structure of Behavioral Acts", Intern J. Neuroscience, 1989, vol. 44, pp. 251-262.

Mullenix, Phyllis J., "Evolution of Motor Activity Tests Into A Screening Reality", Toxicology and Industrial Health, vol. 5, No. 2, 1989, pp. 203-216.

Nelson, M.E., et al., Prey Capture in the Weakly Electric Fish Apteronotus Albifrons: Sensory Acquisition strategies and electrosensory consequences. *J. Exp. Biol.* 202, 1195-1203 (1999).

Norton, Stata, "Amphetamine as a Model for Hyperactivity in the Rat", Physiology & Behavior, vol. 11, pp. 181-186, Brain Research Publications Inc., 1973.

Oliver, N., et al., "LAFTER: Lips and Face Real Time Tracker," 1997, IEEE Computer Society Conference on Computer Vision and Pattern Recognition, San Juan, Puerto Rico, pp. 123-129.

Pavlovic, V., et al., "Visual Interpretation of Hand Gestures for Human-Computer Interaction: A Review," 1997, IEEE Transactions on Pattern Analysis and Machine Intelligence, vol. 19, No. 7, pp. 677-695.

Pavlovic, V.I., et al., Visual Interpretation of Hand Gestures for Human-Computer Interaction: A Review. Dept. of Electrical and Comp. Eng. & the Beckman Inst For Ad. Sci. and Tech., University of Illinois at Urbana-Champaign.

Pear, J.J., et al., Three-dimensional spatiotemporal imaging of movement patterns: Another step toward analyzing the continuity of behavior. *Behavior Res. Methods, Instruments & Computers* 21, 568-573 (1989).

Pentland, A., et al., Modeling and Prediction of Human Behavior. *Neural Computation* 11, 229-242 (1999).

Pentland, Alex, et al., "Modeling and Prediction of Human Behavior", MIT Media Lab Preceptual Computing Technical Report No. 433 (Originally published as: Towards Augmented Control Systems, in IEEE Intelligent Vehicles 95, pp. 350-355, Detroit MI, Sep. 25-26, 1995).

Pentland, Alex, et al., "Real-Time 3-D Tracking and Classification of Human Behavior", Image Understanding Workshop, Defense Advanced Research Projects Agency, vol. 1, May 11-14, 1997, pp. 193-200.

Pentland, Alex, et al., "Toward Augmented Control Systems", Proceedings of the Intelligent Vehicles '95 Symposium, Sep. 25-26, 1995, pp. 350-355.

Puopolo, M., et al., "Continuous time Markov chain models: a useful tool in understanding behavioral patterns", Measuring Behavior '98, $2^{nd}$ International Conference on Methods and Techniques in Behavioral Research (1998). Retrieved from http://www.noldus.com/events/mb98/abstracts/puopolo.htm.

Rabiner, L.R., et al. "An Introduction to Hidden Markov Models", IEEE ASSP Magazine, vol. 3, No. 1, Jan. 1986, pp. 4-16.

Rasnow, B., et al., Applications of Multimedia Computers and Video Mixing to Neuroethology. Retrieved from http://www.bbb.caltech.edu/electricfish/brian/mm/multimedia.html on Jan. 10, 2002, pp. 1-8.

Rehg, J.M., et al., DigitEyes: Vision-Based Hand Tracking for Human-Computer Interaction. *Proc. IEEE Workshop on Motion of Non-Ridgid and Articulated Objects*, Austin, TX 16-22 (Nov. 1994), pp. 1-25.

Rehg, J.M., et al., Visual Tracking of Self-Occluding Articulated Objects. School of Computer Science, Carnegie Mellon University, Pittsburgh, PA 1-37 (Dec. 31, 1994).

Rife, J., et al., "Visual Tracking of Jellyfish in Situ," 2001, IEEE International Conference on Image Processing, Thessaloniki, Greece, pp. 289-292.

Rojas, J.C., et al., (2000). Flight and oviposition behavior toward different host plant species by the cabbage moth, Mamestra brassicae (L.) (Lepidoptera: Noctuidae). Journal of Insect Behavior, 13, 247-254.

Rosin, et al., "Evaluation of Global Image Thresholding for Change Detection", Patent Recognition Letters 24, pp. 2345-2356 (2003).

Rosin, et al., "Image Difference Threshold Strategies and Shadow Detection" Proceedings of the 6th British Machine Vision Conference (1995).

Rousseau, et al., "Classification of rat behavior with an image processing method and a neural network," Behav. Res. Meth. Instr. Comp., 32, 63-71 (2000).

Rousseau, J.B.I., et al., "Classification of rat behavior by a neural network", Poster presented at Measuring Behavior '98, $2^{nd}$ International Conference on Methods and Techniques in Behavioral Research, Aug. 18-21, 1998, Groningen, The Netherlands, pp. 1-2.

Rousseau, J.B.I.,et al, "Automated Observation of Multiple Individually Identified Rats", Poster presented at Measuring Behavior '96, International Workshop on Methods and Techniques in Behavioral Research, Oct. 16-18, 1996, Utrecht, The Netherlands, pp. 1-2.

Rubin, A., Video Laboratories: Tools for Scientific Investigation. *Communications of the ACM* 36, 64-65 (May 1993).

Sams-Dodd, Frank, Journal of Neuroscience Methods, vol. 59, 1995, pp. 157-167.

Scheel, D., Development of an autonomous underwater vehicle for behavioral studies of octopus and other marine animals by video technique. Retrieved from http://marine.alakapacific.edu/octopus/ShadowNSFpro-summary.html on Jan. 10, 2002, p. 1.

Schwarting, R.K.W., et al., A video image analyzing system for open-field behavior in the rat focusing on behavioral asymmetries. *J. Neurosci. Methods* 49, 199-210 (1993).

Schwarting, R.K.W., Measurement of Behavioral Asymmetries in Rodents Using Automated Video Image Analysis. *Measuring Behavior '96* retrieved from http://www.noldus.com/events/mb96/abstract/schwarti.htm on Jan. 14, 2002, p. 1.

Smit, J., et al., "Automatic Recognition of Behavioral Patterns in Rodents Using Digital Imagining", Poster presented at Measuring Behavior '96, International Workshop on Methods and Techniques in Behavioral Research, Oct. 16-18, 1996, Utrecht, The Netherlands, p. 1.

Smyth, P.P., et al., "Automatic Measurement of Vertebral Shape Using Active Shape Models", 3rd IEEE Workshop on Applications of Computer Vision (WACV 1996) p. 176.

Smyth, P.P., et al., "Automatic Measurement of Vertebral Shape Using Active Shape Models," Depts. of Medical Biophysics & Diagnostic Radiology, University of Manchester, pp. 705-714.

Spink, A.J., et al., "EthoVision color identification: A new method for color tracking using both hue and saturation," 2000, Measuring Behavior Conference, Nijmegen, The Netherlands, pp. 295-297.

Spratt, M., "Approaches to Automating Analysis Of Motion Data for Ethology", Poster presented at Measuring Behavior '96, International Workshop on Methods and Techniques in Behavioral Research, Oct. 16-18, 1996, Utrecht, The Netherlands, p. 1.

Spratt, M., An Introduction to Automated Ethology and Autonomous Systems or the Ethology of Ethologists. S8—*Stock Behavior Measures for Success* J. Muir & F. Sevila, eds. 182-183 (Feb. 1994).

Spruijt, B.M. (1991). An ACTH(4-9) analog enhances social attention in aging rats: a longitudinal study. Neurobiology of Aging, 13, 153-158.

Spruijt, B.M., et al., "Automatic behavior recognition: what do we want to recognize and how do we measure it?", Paper presented at Measuring Behavior '98, 2nd International Conference on Methods and Techniques in Behavioral Research, Aug. 18-21, 1998, Groningen, The Netherlands, pp. 1-2.

Spruijt, B.M., et al., "Behavioral Sequences as an Easily Quantifiable Parameter in Experimental Studies", Physiology & Behavior, vol. 32, pp. 707-710, 1984.

Spruijt, B.M., et al., Consequences of the Ongoing Automation of the Observation and Analysis of Animal Behaviour. *Measuing Behavior '96* retrieved from http://www.noldus.com/events/mb96/abstracts/sprujit.htm on Jan. 14, 2002, p. 1.

Spruijt, Berrie M., et al., "Prolonged Animal Observation by Use of Digitized Videodisplays", Pharmacology Biochemistry & Behavior, vol. 19, pp. 765-769, 1983.

Stitt, J.P., et al., Automated Analysis of Feeding Behavior in Small Animals. IEEE 120-122 (1998), pp. 1-3.

Sumpter, N., et al., Modeling Collective Animal Behaviour using Extended Point-Distribution Models. School of Comp. Studies, Res. Report Series, University of Leeds, Report 97.24 (May 1997), pp. 1-13.

Tang, L., et al., Automatic analysis of the behaviour of group-housed pigs by an image collection system. *Measuring Behavior '98* retrieved from http://www.noldus.com/events/mb98/abstracts/tang.htm on Jan. 14, 2002, p. 1.

Torello, M.W., et al., An Automated Method for Measurement of Circling Behavior in the Mouse. *Pharmacol. Biochem. & Behav.* 19, 13-17 (1983).

Ueda, et al., "Automatic Structure Visualization for Video Editing", Interchi '93 Conference Proceedings (1993).

Van Den Berg, Caroline, L., et al., "Sequential Analysis of Juvenile Isolation-Induced Decreased Social Behavior in the Adult Rat", Physiology & Behavior, vol. 67, pp. 483-488 (1999).

Van Gelder, Russell N., et al., "Real-Time Automated Sleep Scoring: Validation of a Microcomputer-Based System for Mice", Sleep, 14 (1); pp. 48-55, 1991.

van Lochem, P.B.A., et al., Automatic recognition of behavioral patterns of rats using video imaging and statistical classification. *Measuring Behavior 1998* retrieved from http://www.noldus.com/events/mb98/abstracts/lochem2.htm on Jan. 14, 2002, pp. 1-2.

van Lochem, P.B.A.,et al., "Video tracking: improved methods for identification of animals with color markers", Poster presented at Measuring Behavior '98, 2nd International Conference on Methods and Techniques in Behavioral Research, Aug. 18-21, 1998, Groningen, The Netherlands, p. 1.

Wilson, Andrew, D., et al., "Recovering the Temporal Structure of Natural Gesture", Automatic Face & Gesture Recognition, Automatic Face and Gesture Recognition, Proceedings of the Second International Conference (1996).

Wolf, "Key Frame Selection by Motion Analysis", IEEE, pp. 1228-1231, (1996).

Wolf, Wayne, "Hidden Markov Model Parsing of Video Programs", 1997 IEEE International Conference on Acoustics, Speech and Signal Processing, vol. IV of V, Apr. 21-24, 1997, pp. 2609-2611.

Yang, M.-H., et al., Extraction and Classification of Visual Motion Patterns for Hand Gesture Recognition. *Proc. IEEE CVPR* 892-897 (1998).

"Biobserve—Spectator", http://www.biobserve.com/software/spectator/index.html, printed on Jan. 14, 2002, pp. 1-5.

"Current Research: Characterising Behavioural Phenotypes Using Automated Image Analysis", http://www.wiau.man.ac.uk/~ct/research.html, printed on Jan. 14, 2002.

Current Research: Characterizing Behavioural Phenotypes Using Automated Image Analysis. Retrieved from http://www.wiau.man.ac.uk/~ct/research.html on Jan. 14, 2002, pp. 1-4.

Environment and Behavior Symposium, "The Use of Computers for Modeling, Recognizing and Recording Behavior", J. Anim. Sci. 137 (1997).

Environment and Behavior Symposium: The Use of Computers for Modeling, Recognizing and Recording Behavior. *J. Anim. Sci.* 75(Suppl. 1) (1997).

EthoVision: Video tracking system for automation of behavioral experiments. Retrieved from http://www.noldus.com/products/ethovision/ethovision.html on Jan. 14, 2002, pp. 1-2.

"Etho Vision", Index Page from http:/www/noldus.com/products/ethovision.html, printed on Jan. 14, 2002, pp. 1-2.

LIC—Animal activity monitoring. Retrieved from http://www.licmef.com/animalactivitymonitoring.htm on Jan. 10, 2002, pp. 1-2.

"Measurement of Behavioral Asymmetries in Rodents Using Automated Video Image Analysis", http://www.noldus.com/events/mb96/abstract/schwarti.htm, printed on Jan. 14, 2002, p. 1.

"Measuring Behavior '96", http://www.noldus.com/events/mb96/mb96.htm, printed on Jan. 17, 2002, pp. 1-2.

"Measuring Behavior '96—Posters", http://www.noldus.com/events/mb96/abstract/posters.htm, printed on Jan. 17, 2002, pp. 1-4.

Motion Capture from Video. Retrieved from http://www.cse.ucse.edu/~wilhelms/fauna/Vision on Jan. 10, 2002, pp. 1-2.

Multiple Animal Movement Analyzer (MAMA) Manual. Retrieved from http://www.ifas.ufl.edu/~damaweb/mama.html on Jan. 10, 2002, pp. 1-5.

*Neuroscience* retrieved from http://www.tracsys.com.uk/Pages/Neuroscience/neuromain.htm on Jan. 10, 2002, pp. 1-12.

Noldus Information Technology releases The Observer 3.0. Retrieved from http://www.noldus.com/site/popupdoc.php?doc=200407115&print= 1& (1993).

"Noldus to Develop New Technology for Automated Behavorial Phenotyping", Press Release: Neuro Bsik Project, www.noldus.com/press/pr04_neurobsik.html (2004).

Observe and Analyse Behavior. *Biobserve* retrieved from http://www.bioserve.com/software/spectator/index.html on Jan. 14, 2002, pp. 1-4.

Poly-Track: Video Tracking System. *San Diego Instruments* Retrieved from http://www.sd.inst.com/polytrk.htm on Jan. 10, 2002, pp. 1-3.

The GEDRI Project: Quantitative analyses of sexual behaviour, as a screening tool of hormone-mimicking effects on animal reproduction. Retrieved from http://endocrine.ei.jrc.it/qedri/pack_edri.FullScreen?p_rs_id=3 on Jan. 10, 2002, p. 1.

The Observer: Professional system for collection, analysis and management of observational data. Retrieved from http://www.noldus.com/products/observer/observer.html on Jan. 14, 2002, pp. 1-2.

*The Mostert Group* retrieved from http //www.mostertgroup.com on Jan. 10, 2002, pp. 1-3.

Trackit System Family. *Biobserve* retrieved from http://www.biobserve.com/software/trackit/index.html on Jan. 10, 2002, pp. 1-3.

VideoScan-2002 Image Analysis System. Retrieved from http://www.accuscan-usa.com/ezvideo.htm on Jan. 10, 2002, pp. 1-10.

Visual Fusion 3D Tracking and Motion Analysis. Retrieved from http://www.swcp.com/~spsvs/VisualFusion/visfusInitial.html on Jan. 10, 2002, p. 1.

Watermaze Tracking. *Acimetrics Software* retrieved from http://www.actimetrics.com/watermaze/tracking.html on Jan. 10, 2002, p. 1.

U.S. Appl. No. 10/147,336, filed May 15, 2002, Brunner et al.

* cited by examiner

Chlordiazepoxide 1.25 mg/kg

| Behavior after<br>Behavior before | Rear | Directed burying | Contact probe | Digging | Approach | Locom. | Groom | Immob. |
|---|---|---|---|---|---|---|---|---|
| Rear | 31.56 | 4.56 | 7.86 | 9.00 | 6.20 | 8.74 | 7.24 | 2.54 |
| Directed burying | -0.30 | | -0.25 | -1.00 | -1.81 | 0.19 | -1.00 | 0.62 |
| Contact with probe | 14.75 | -1.50 | -0.62 | -1.00 | -3.28 | -0.67 | -1.00 | -1.43 |
| Digging | 0.16 | 3.17 | | | -1.00 | 0.27 | | -0.25 |
| Approach | 3.32 | -2.71 | -2.18 | -1.06 | -3.63 | -1.80 | -1.96 | -2.75 |
| Locomotion | 8.23 | -1.26 | 0.62 | -0.52 | -3.47 | | 3.67 | 0.13 |
| Grooming | | | | -1.50 | | 3.68 | | -1.14 |
| Immobile | 7.86 | -1.63 | | -0.57 | -0.17 | 0.18 | 1.45 | |

CPMC 2.5 mg/kg

| Behavior after<br>Behavior before | Rear | Directed burying | Contact probe | Digging | Approach | Locom. | Groom | Immob. |
|---|---|---|---|---|---|---|---|---|
| Rear | -1.77 | -2.83 | 0.94 | 2.83 | 2.83 | 1.06 | -2.83 | -2.39 |
| Directed burying | -2.83 | | -2.83 | -1.89 | -2.83 | 10.18 | | |
| Contact with probe | -2.42 | -2.83 | 1.41 | 0.00 | 0.00 | -2.36 | -2.59 | -1.13 |
| Digging | 2.83 | 16.97 | -2.83 | | -1.99 | 6.69 | -2.83 | |
| Approach | 0.00 | | 0.00 | -2.16 | 28.28 | 0.71 | -2.83 | 0.61 |
| Locomotion | 0.00 | 3.64 | 0.94 | 6.17 | 48.08 | -2.83 | 5.66 | 11.31 |
| Grooming | | | | -0.35 | -2.83 | 1.65 | -2.83 | -0.77 |
| Immobile | 5.66 | 9.90 | | 2.12 | | 4.53 | 0.71 | -2.83 |

Fig. 13

METHOD FOR PREDICTING TREATMENT CLASSES USING BEHAVIOR INFORMATICS

RELATED APPLICATIONS

This application is a continuation of U.S. Nonprovisional application Ser. No. 11/741,312 now U.S. Pat. No. 7,580,798 filed Apr. 27, 2007, which is a continuation of U.S. Nonprovisional application Ser. No. 10/147,334 filed May 15, 2002, now U.S. Pat. No. 7,269,516, which claims priority to U.S. Provisional Application No. 60/291,039 filed May 15, 2001 and to U.S. Provisional Application No. 60/326,271 filed Oct. 1, 2001, the specifications of which are incorporated by reference in their entirety herein.

FIELD OF THE INVENTION

This invention generally relates to systems and methods that capture behavioral and physiological data into a database and to systems and methods that analyze and extract relevant and new information from the database. More particularly the invention relates to a method used to capture, summarize and register animal movements and physiological measurements, and to a database mining tool that will allow high throughput analysis of drugs effects, and characterization of animals of different strains and genetically manipulated animals.

BACKGROUND OF THE INVENTION

During the last decade new enabling technologies in molecular biology, chemistry, automation, and information technology have dramatically reshaped pharmaceutical and biological research. The completion of the sequencing of the genome in humans and mice has opened new opportunities to study the relationship between gene expression and behavioral function. Although the function of many genes is being unraveled resulting in many promising therapeutic targets, progress in understanding neuropsychiatric disorders is lacking.

In vivo behavioral biology is needed to validate behavioral phenotypes associated with newly discovered genes and new drug leads. As it is a slow, labor-intensive, high-maintenance technique it creates a bottleneck, and creates a need for a novel paradigm with a new approach to modern, scalable and automated technology.

Drug Discovery

The development of new drugs and medications involves the study of their effects on various animals. The use of mice, dogs and other animals for experimental purposes is needed to obtain data so that subsequent tests on humans may be safely carried out.

Assessing behavior and the effects of drugs on laboratory animals has been a central component of the field of neuropharmacology. The discovery of chlorpromazine, for example, as a drug that produces differential effects on avoidance and escape behavior provided a strong impetus for evaluating the behavioral effects of experimental antipsychotic drugs. The growth of neuropharmacology coincided also with the development of the field of operant conditioning. Indeed, many of the techniques used to control and monitor operant behavior were enthusiastically endorsed by behavioral pharmacologists. It is recognized nowadays that the assessment of behavior in determining the effects of drugs is of pivotal importance.

Phenotype/Genotype Correlation

With the completion of the genome sequence in both humans and mice, a wealth of information has inundated the scientific community Thousands of genetically manipulated animals are being generated in hundreds of different laboratories for many different purposes. Although the research in academia and industry focusing on the function of genes is normally hypothesis driven, most of the time there are secondary adaptations ("side effects") that confound or obliterate the targeted gene function. For example, a gene involved in memory may result in abnormal sensory function, and therefore many tests for the assessment of memory may have to be ruled out, if they depend on the sensory function affected. The difficulty is that laboratories that develop these genetically manipulated animals rarely have the capacity to test for secondary adaptations and most of these may go unnoticed.

In the area of functional genomics there is therefore a special need for a comprehensive assessment of behavior that brings the ability to correlate behavior, physiology and gene expression and allows to rule out secondary adaptations as the cause of observed behavioral and physiological phenotypes.

Standard Behavioral Techniques

Although great progress has been made in the development of techniques that permit objective and quantitative study of behavior, these techniques involve considerable expertise and effort. In the field of neuropharmacology, for example, the adoption and widespread use of these procedures has had the multiple benefit of broadening our understanding of the principles governing behavior, elucidating the mechanisms of drug action, and demonstrating the complex neurochemical substrates influencing both behavior and drug action. However, these behavioral techniques are time consuming, they provide a limited picture of the animal's behavior and do not allow a comprehensive assessment of the test subject. The type of behavioral assessment currently used is limited by the choice of the end point measures or dependent variables, and by the limitation of the observation to a given period. Behavioral data are therefore limited to and by what the scientific community considers a relevant variable, by the way this variable is measured, and by the context and time constraints of the testing.

Behavioral data are collected using a myriad of different techniques. In some cases, drug-induced behavior is assessed by trained observers who employ rating scales. Although a trained observer can detect complex and/or subtle changes in behavior, there is an intrinsic variability and subjectivity in the behavioral data generated in this way. Reliability of the data heavily depends on the expertise of the observer. This method is obviously constrained by the short duration of the observation.

In drug research, for example, various devices are often used for measuring the activity of a test animal treated with an experimental substance. Normal activity of untreated animals is measured to provide a comparison with the results from treated animals. Measurements of activity are usually done with scientific equipment for continuously monitoring an animal's movement within a confined area. Whereas these devices permit prolonged observation of the animal's activity, other concurrent behaviors are normally ignored.

Various types of animal activity monitors have been used by behavioral analysts to study the effects induced upon the animal by experimental drugs. Such monitors include, for example, video equipment and light sensors. These types of monitors have been limiting in the study of animal behavior because they only allow the dimension the animal's visually detectable gross motion activities such as, for example, locomotion and stereotyped motor behavior. Complex behavioral assessment data is unavailable from these types of monitors.

An additional problem in the study of animal behavior using conventional methods is that the test subject is usually transported from the colony room to a test area or cage, in a different room, where the behavioral studies are conducted. This removal involves handling the test subject, placing it on a cart and rolling the cart away, and placing it in a different environment. This procedure by itself has profound influences on the animal's behavior thereby affecting the results. If processes related to stress, for example, are to be avoided, this movement of animals from one setting to another is clearly counterproductive.

Thus, in both the area of functional genomics and in drug discovery, there remains a need in the art for an apparatus and method that provides assessment of animal's behavior beyond mere gross motor activities. A comprehensive assessment over long or short periods of time is required. Such assessment can include what type of activity is performed, its intensity, frequency and duration, how these parameters change over time, and what complex patterns that involved a succession of different behaviors can be detected. A system that can link these measurements to telemetric devices measuring blood pressure, heart rate and other physiological parameters in parallel to the acquisition of behavioral data will be invaluable. In addition, there is a need to provide a method to reduce the level of manipulation of the test subject.

SUMMARY OF THE INVENTION

The present invention relates to systems and methods for massively parallel data acquisition and analysis of behavior in a manner which permits integration of behavioral data with genomics, through the use of robotics and bioinformatics.

One aspect of the present invention relates to novel robotic hardware to collect and record a plurality of experimental behavioral, biochemical, neurological and physiological information from animals. Another aspect comprises computer vision, preferably in combination with other algorithms to extract behavioral/physiological states and to extract temporal and other structures from said plurality of information. A third aspect of the present invention relates to a computer system for mining said information for identifying a pattern reflecting the effects of drug, environmental or genetic manipulation of the test animals or subjects. In general, the preferred system ideally includes:

(i) equipment to mechanically and visually record one or more behavioral, neurological, biochemical and/or physiological measurements using a variety of video cameras and other sensors; (ii)

software utilizing computer vision and additional algorithms to extract one or more behavioral, neurological, biochemical and/or physiological states from said measurements;

(iii) one or more behavioral, neurological, biochemical and/or physiological measurement databases including information representative of animal behavior, neurology, biochemical and/or physiology observed from previous experiments with a) animals treated with drugs, b) having predetermined genetic traits and/or c) having otherwise been exposed to an environmental cue or any other type of treatment different from normal, control and/or sham-treated animals;

(iv) a query server program that receives query behavioral, neurological, and physiological data from one or more users of the system;

(v) a database searching program that (a) compares query behavioral, neurological and physiological data with a model derived from said previous animal experiments represented in said behavioral, neurological, and physiological measurement database(s), and (b) correlates the query data with behavior of animals treated with other drugs and/or having predetermined genetic traits; and (vi) a reporting program that interfaces with the user for reporting to said user information representative of the degree of correlation, if any, between said query behavioral, neurological, and physiological data and entries in said measurement database(s).

In certain embodiments, the subject system may be described in terms of main components, comprising a data capture system for capturing behavioral and other animal derived data, intelligent software such as computer vision algorithms, that capture and/or identify behavioral/physiological states, and a custom-built intelligent database that enables sophisticated statistical analysis of the captured states and data mining. The data capture system advantageously can be a free-standing module that either is, or fits into, a standard laboratory home cage and can be fitted with mechanical devices for conducting experiments. It may be equipped with a variety of sensors that automatically record the test subject's activity and biological changes and feed them to the computer system on a continuous real-time basis. A variety of mechanical challenges advantageously part of the systems, can be computer-controlled for conducting a range of standardized, scientifically validated tests. Physical activity can be captured by a highly sensitive movement capture system that allows for minutely detailed analysis.

Another aspect of the invention relates to the complementary use of software to classify acquired behavioral, neurological, biochemical and physiological data into predetermined states, such as an a-priori defined sleeping state, in addition to identifying novel states that may be present in the complex datasets captured by the system.

The test data can also be time stamped and sent directly to the database for further retroactive processing.

Another aspect of the invention comprises a relational database whereby a plurality of data can be compared with reference data and other data from linked databases. In certain instances, information from the system, may be advantageously linked with data from public and private sources to provide an exceptionally powerful platform for analysis.

In an exemplary embodiment, the subject method and system is used to categorize drugs based on their "signatures". In the standard behavioral lab many different tests are implemented to study the full profile of a drug or to characterize a knockout. A drug is qualified, for example, as an anxiolytic if it increases some responses (e.g., exploration of the open arms of the elevated plus maze), decreases other (e.g., freezing) and shows no major non-specific side effects that may confound the interpretation (e.g., sedation). Behavioral scientists therefore understand the therapeutic value of a drug through the definition of a profile, which we call here a drug signature. One could also think about signatures of similar kind for genetically altered mutants or animal models, or even lesions (e.g., cerebellar-dysfunction signature).

Another aspect of the invention relates to a computer-implemented method for identifying potential modes of action of a candidate drug. The subject computer-implemented method includes providing a computer controlled system such as that described previously including:

(i) signatures comprising one or more behavioral, neurological, and physiological measurement databases including information representative of animal behavior, neurology and physiology observed for previous experiments with animals a) treated with drugs, b) having predetermined genetic traits and/or c) having otherwise been exposed to an environmental cue or any other type of treatment different from normal, control and/or sham-treated animals;

(ii) a query server program that receives query data from one or more users on the system;

(iii) a database analysis program that
(a) compares query behavioral, neurological, and physiological data with the signature derived from said previous animal experiments represented in said measurement database(s), and
(b) correlates the query data with said signatures; and (iv) a reporting program that generates reports including information representative of the degree of correlation, if any, between said query data and entries in said measurement database(s).

Access to the computer system is provided to users to input query behavioral data. The method preferably also includes the capability of reporting correlations, if any, between said query behavioral data input by said user and activity of other drugs and/or genetic traits.

Still another aspect of the present invention relates to a method for predicting potential modes of action of a test compound. In general the method relies on access to, such as by generating, a database of information representative of behavioral, neurological, biochemical and physiological measurements from animals previously treated with drugs, or those having predetermined genetic traits and/or which have otherwise been exposed to at least one environmental cue or any other type of treatment which differs from that experienced by normal, control and/or sham-treated animals. From the database, a set of predictor variables, or signatures, are generated which define said information in said database, said set of predictor variables defining correlations between said behavioral, neurological, and physiological measurements and said drugs, predetermined genetic traits and/or exposure to environmental cues. This can be used to derive a model that represents a probability relationship between a response of an animal to a test compound and said set of predictor variables, said relationship derived through using at least one automated non-linear algorithm or other bioinformatics analysis tool. The model may advantageously be used to predict potential therapeutic application of a test compound based on behavioral, neurological, and physiological measurements from one or more animals treated with said test compound.

Yet another aspect of the invention relates to a method for predicting potential modes of action of an environmental or genetic effect on an animal. The method includes generating a database of information representative of behavioral, neurological, and physiological measurements from animals treated with drugs, having predetermined genetic traits and/or have otherwise exposed to an environmental cue or any other type of treatment different from normal, control and/or sham-treated animals. From the database(s), a set of predictor variables are generated which define said information in said database, said set of predictor variables defining correlations between said behavioral, neurological, and physiological measurements and said drugs, predetermined genetic traits and/or exposure to environmental cues. A signature may then be derived that represents a probability relationship between (a) behavioral, neurological, biochemical and/or physiological measurements of an animal exposed to a test environmental effect or possessing a predetermined genetic state, and
(b) said set of predictor variables.

Preferably, the relationship is derived through using at least one automated non-linear algorithm. The instant invention may be used to predict potential modes of action of an environmental or genetic effect on a test animal based on behavioral, neurological, and physiological measurements from one or more of said test animals. For instance, the method may be advantageously used for one or more purposes of assessing potential therapeutic effects of a drug, assessing potential toxic side effects of a drug, predicting potential effects of a lesion, predicting potential effects of acute, subchronic (e.g., 2-5 days) or chronic (e.g., more than 5 days) environmental manipulation on fetal, juvenile or adult animals, and predicting potential effects of mutagenesis (natural or artificial, e.g., by chemical or radiation) manipulation of genes (e.g., by transgenic modification, including knock-in, knock-out and knock-down phenotypes).

Another aspect of the invention provides a service for administering, over a wide area network, access to data mining models for identifying potential modes of action of a candidate drug. The subject service includes providing a server system, in communication with a wide area network. Such server systems include one or more behavioral, neurological, and physiological measurement databases including information representative of animal behavior, neurology and physiology observed for previous experiments with animals treated with drugs, having predetermined genetic traits and/or have otherwise exposed to an environmental cue or any other type of treatment different from normal, control and/or sham-treated animals. It may also include a query server program that receives query data from one or more users on the system, and a database-searching program that compares query behavioral, neurological, and physiological data with a model derived from said previous animal experiments represented in said measurement database(s), and correlates the query data with entries in said measurement database(s). In preferred embodiments, the server system will also include a reporting program that generates reports including information representative of the degree of correlation, if any, between said query data and entries in said measurement database(s). These databases and programs can be located on the same or different computers or storage devices. The subject method allows users to employ a client process operating on a client station to connect to said server system through the wide area network and to input query behavioral data. The system can be set up to report to the user(s) correlations, if any, between said query behavioral data input by said user and activity of other drugs and/or genetic traits.

Still another aspect of the present invention provides a method for conducting a drug discovery business. In certain embodiments, the method includes the steps of:

(i) obtaining representative behavioral, neurological, biochemical and/or physiological data of one or more animals treated with a test compound;

(ii) comparing the obtained data with one or more signatures that represent a probability relationship between a response of an animal to a test compound and a set of predictor variables which define correlations between observed behavior and known drugs and/or predetermined genetic traits, said relationship derived through using at least one automated non-linear algorithm or other data analysis process;

(iii) determining, from the comparison data of step (ii), potential modes of action or therapeutic applications of the test compound, and assessing the suitability of further clinical development of the test compound.

The drug discovery business method may advantageously include the additional step of licensing to a third party rights to the test compound for further development. In addition, the subject method may further include formulating a pharmaceutical preparation including one or more agents identified as having a desired therapeutic and/or toxic profile. In certain embodiments, the subject method may advantageously include additional steps of licensing such identified pharmaceutical preparations to third parties and/or establishing a distribution system for distributing the pharmaceutical preparation for sale, and/or may further include establishing a sales group for marketing the pharmaceutical preparation. In another drug discovery business embodiment, the subject systems and bioinformatics database can be made available to one or more third parties under a licensing or other scheme ideally involving milestone payments and/or a percentage of the future revenues of drugs identified using the systems of the instant invention.

In additional embodiments, for compounds selected for further clinical development, the method can include conducting therapeutic profiling of the test compound, or analogs thereof, for efficacy and toxicity in animals.

Yet another aspect of the present invention provides a method for conducting a drug discovery business, and advantageously makes use of the hardware and computer system described above. For instance, the subject method can include obtaining one or more sets of behavioral, neurological, biochemical and physiological data for one or more animals treated with a test compound. Accessing the subject computer system, e.g., as described supra, one receives information representative of the degree of correlation, if any, between behavioral, neurological and/or physiological data for said test compound and entries in said measurement database(s) or signatures or signatures derived therefrom. At least in part from the correlation step the method may advantageously determine potential modes of action of the test compound, and assesses the suitability of further clinical development of the test compound for various therapeutic applications. For compounds selected for further clinical development, one can (optionally) conduct therapeutic profiling of the test compound, or analogs thereof, for efficacy and toxicity in animals. In certain preferred embodiments, the method also includes a step of formulating a pharmaceutical preparation including one or more agents identified as having a desired therapeutic and/or toxicity profile.

Another aspect of the present invention provides a method for conducting a drug discovery business, in which the following steps are included:

(A) providing personnel for obtaining behavioral data from one or more animals treated with a test compound;

(B) providing a data mining system for analyzing the behavioral, neurological, biochemical and physiological data, said system comprising:

(i) one or more behavioral, neurological, biochemical and physiological measurement databases including information representative of animal behavior observed from previous experiments involving animals a) treated with drugs, b) having predetermined genetic traits and/or c) have otherwise been exposed to an environmental cue different from that experienced by normal, control and/or sham-treated animals;

(ii) a query server program that receives query behavioral, neurological, biochemical and/or physiological data from one or more users on the system;

(iii) a database searching program that (a) compares query behavioral, neurological, biochemical and/or physiological data with a signature comprising behavioral, neurological, biochemical and/or physiological data from said measurement databases, and (b) correlates the query behavioral, neurological, biochemical and/or physiological data with said signatures of animals treated with other drugs and/or having predetermined genetic traits; and (iv) a reporting program that generates reports including information representative of the degree of correlation, if any, between said query behavioral, neurological, biochemical and/or physiological data and entries in said behavior signatures;

(C) determining, using the system of (B), potential modes of action of the test compound, and assessing the suitability of further clinical development of the test compound;

(D) for compounds selected for further clinical development, conducting therapeutic profiling of the test compound, or analogs thereof, for efficacy and toxicity in animals; and (E) formulating a pharmaceutical preparation including one or more compounds identified in step (D).

In embodiments where the subject methods and systems are used for preclinical research, the focus may include gene target identification and validation, synthesizing and extracting compounds, compound selection and toxicity testing.

In certain embodiments, the compounds can be further analyzed using the standard tests which may include, for example, elevated plus maze, open field, dark-light transition test, tail suspension, forced swim test, Morris water maze, etc.

In certain preferred embodiments of the subject systems and methods, the model is a hidden Markov model. In other embodiments, the model is a neural net.

In certain preferred embodiments of the subject systems and methods, the database(s) include behavioral, neurological, biochemical and physiological data representative of one or more of sleeping, grooming, locomotion (including ambulatory and non-ambulatory movements, foot misplacement, and the like), rearing, stereotypic behavior, digging, anxiety, intake, pain sensitivity, convulsions, learning, memory (short/long), task switching, attention, discrimination, motivation, response inhibition, reward sensitivity, avoidance, startle, tolerance and withdrawal.

In certain preferred embodiments of the subject systems and methods, neurological data is acquired, and may include one or more of EEG data, data concerning changes in CNS structures and/or function (including size and location of necrotic tissue), occurrence of seizures, level of blood flow to CNS tissue, glucose consumption by CNS tissue, oxygen consumption by CNS tissue, somatosensory evoked potentials (SSEPs), intracellular current flow, and information from other imaging sources including magnetic resonance imaging (MRI), computed tomography (CT), positron emission tomography (PET), single photon emission computed tomography (SPECT), somatosensory evoked potentials (SSEPs), and magnetoencephalography (MEG).

In certain preferred embodiments of the subject systems and methods, the physiological data includes one or more of gut motility data, body weight data, temperature data, EKG cardiac response data (e.g., output, QT interval), and respiration data (e.g., rate, $O_2$ and/or $CO_2$).

In certain preferred embodiments, the database includes one or more of gene transcriptional data (such as transcription profiles), proteomics data (e.g., data on protein and protein expression levels, occurrence of post-translational modifications, cellular localization, protein-protein interactions, etc), marker profiles, and metabolite data.

In certain preferred embodiments of the subject systems and methods, the database(s) is an annotated database including information representative of the mechanism of action of drugs for which behavioral, neurological, biochemical and physiological information has been included in the database.

In certain embodiments, the present invention is directed to an automated, rapid throughput, in vivo behavioral assay systems with associated bioinformatics, e.g., to assess spontaneous and conditioned behavior in rodents. To this end, the invention provides systems and methods for use in the assessment of behavioral, neurological, biochemical and physiological characteristics that can depend on innate characteristics of an animal, such as different genetic backgrounds or genetic manipulations, as well as environmental cues, such as drug treatment. The invention also provides systems for generating and maintaining databases of relevant behavioral, neurological, biochemical and physiological models that can be used for information mining, for example, to uncover associations, patterns, and trends in drug response or genetic profiles, as well as cluster and classify information about drug effects, and to develop predictive models.

In certain preferred embodiments, the subject invention provides rapid-throughput, automated animal testing systems, using hardware and software that permits continuous collection of behavioral, neurological, biochemical and physiological data. In contrast to traditional preclinical behavioral, neurological, biochemical and physiological testing processes, the automated systems of the present invention can be more efficient, reproducible, cost-effective and operator-independent, as well as compatible with modem tools for drug discovery. Continuous and automated character of the data collection process, for example, can increase the statistical power and ability to find unbiased embedded correlations or "behavioral, neurological, biochemical and physiological signatures" in the data.

Another aspect of the invention provides reference data sets providing behavioral, neurological, biochemical and/or physiological responses to compounds and/or genetic manipulations of animals. In preferred embodiments, the invention provides an extensive and continuously updated reference database and relational software tools that can be used to characterize the behavioral, neurological, biochemical and/or physiological impact of compounds and genetic manipulations and enable users to perform automated and intelligent analyses of its behavioral, neurological, biochemical and/or physiological function, benchmark these against previously assembled reference database, and use these to make predictions about therapeutic efficacy and safety. Accurate prediction of therapeutic efficacy and potential side-effects accelerates lead selection and drug development and reduces costs.

The subject methods and systems can be used as part of a discovery program for new therapeutic candidates and of unanticipated neurological and psychiatric applications for drugs that were previously investigated in other therapeutic areas. Other drug-related observations which advantageously can be determined by datamining the databases of the present invention include:

interactions among over-the-counter (OTC) medicines
  interactions between prescription and OTC medicines
  interactions among ethical medicines
  interactions between any kind of medicine and various foods, beverages, vitamins, and mineral supplements
  common characteristics between certain drug groups and offending foods, beverages, medicines, etc.
  distinguishing characteristics among certain drug groups (e.g., for some people, certain antihistamines may not produce an adverse reaction to certain foods, and therefore may be a better choice among the large number of antihistamines on the market)
  questionable interactions based on very limited evidence, but which may be of great interest (e.g., a few users out of many thousands of users report a serious, but unusual side effect resulting from some combination of characteristics) and
  determining which types of patients are likely to be at risk when using a particular medicine.

Yet another aspect of the invention provides a module for collecting physical and biological data concerning a test subject. The module further communicates with a processor that interprets the data to capture and time-stamp the behavior of the test subject. In accordance with another embodiment of the invention, an apparatus and method is provided for automated recording of animal behavior and interpretation of the observations by using individual modules, multiple modules or modules with multiple channels. Another advantage of the instant invention, particularly when multiple apparatuses are used is that a large number of animals may be observed simultaneously, thereby dramatically leveraging the efficiency of laboratory personnel. Animals observed at the same time may be part of the same experiment or a variety of different experiments. The system and method also allows hypothesis and validation of test animal behavior when the test animal is exposed to manipulation and/or an experimental drug, or when genetically manipulated animals are studied.

The apparatus and method used to assess animal behavior includes a module having one or more sensors that collectively obtain a variety of behavioral, neurological, biochemical and/or physiological and physiological data from a test subject. The sensors of the apparatus also may provide for the ability to simultaneously obtain data pertaining to different overt activities or movements and to physiological responses of the test subject. One embodiment would provide a portable module that fits into standard laboratory cages thereby permitting behavioral, neurological, biochemical and/or physiological testing in the animal's own habitat, but other designs are possible including where the module is the cage. Multiple-dimensional modeling of the test subject based on the system's interpretation of the data allows pattern recognition of the drug signature, predictive drug analysis, and interpretation of the phenotype of a genetically engineered animal.

These and other aspects, features, and advantages of the present invention are further described in the following Detailed Description, which is to be read in conjunction with the accompanying drawings.

BRIEF DESCRIPTION OF THE DRAWINGS

FIG. 13 shows exemplary data from an experiment in which mice were treated with one of the indicated drugs ensuing behavior was recorded and later coded by human observers FIG. 14 provides a schematic representation of one embodiment of the data handling modules of a preferred system.

DETAILED DESCRIPTION OF THE INVENTION

I. Overview

Figure 1:
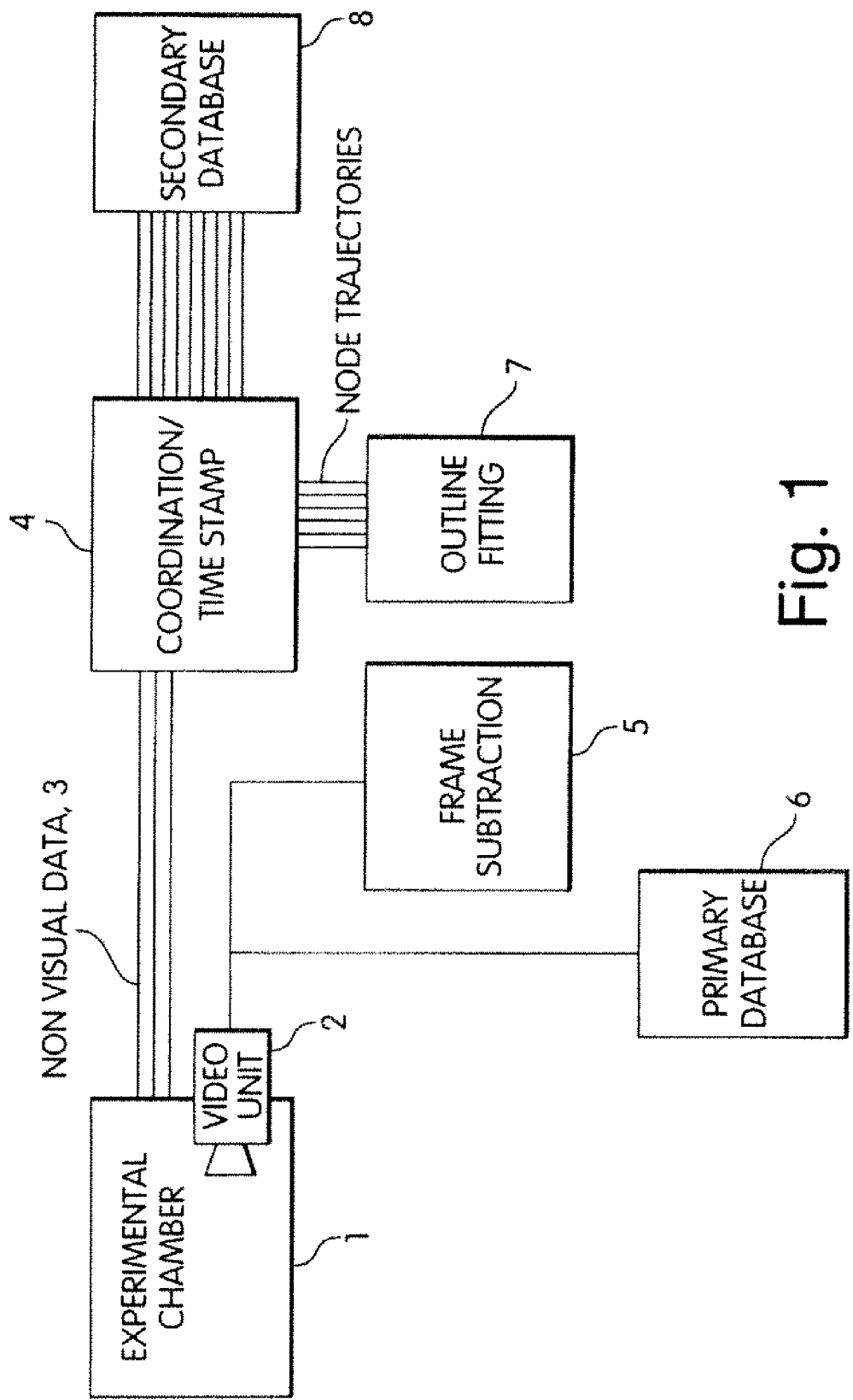
FIG. 1 is a perspective view depicting elements of the system in accordance with one embodiment of the invention.

The invention provides a method, apparatus and data analysis method for massively parallel behavioral, neurological, biochemical and/or physiological data acquisition, analysis, storage and data mining capacity.

Using combinations of machine learning, statistical analysis, modeling techniques and database technology, the subject method advantageously utilizes data mining techniques to find and identify patterns and subtle relationships in animal data that permits inference of rules for the prediction of drug effects.

In many embodiments, the subject methods and systems bring greater precision to behavior analysis compared to traditional behavior testing methods. By automating and systematizing the way in which behavior is captured and collected, the subject systems can be used to standardize the translation and interpretation of visual data, preferably in combination with physiologic data, enabling this information to be stored into a relational database (along with non-visual data also captured during the screening) for analysis. Furthermore, by having the ability to store and compare the captured data in a standardized format, the present method enables the generation of databases related to CNS functions and disorders unparalleled in content. This can greatly increase accuracy and facilitate interpretation of the screening process by providing a strong foundation for comparative analysis.

CNS disorders include mood disorders such as anxiety and depression, psychotic conditions such as schizophrenia, Attention Deficit Disorder (ADD) and Attention Deficit HyperActivity Disorder (ADHD), Alzheimer's disease, migraine, epilepsy, Multiple Sclerosis and Amyotrophic Lateral Sclerosis ("ALS" or Lou Gehrig's Disease). Exemplary CNS disorders that can be modeled by the subject method include 1 Anxiety disorders Mania Depression Neurodegenerative disorders Schizophrenia Addiction ADHD/Impulsivity Pain Eating disorders (obesity) Epilepsy Cognitive disorders (e.g. Neuromotor disorders Alzheimer's Disease, Dementia) Aggression Sleep disorders Sexual disorders It is estimated that certain embodiments of the subject system can reduce the CNS drug discovery process by up to three years and generate better choices of candidates for drug development due to the following:

Throughput that is 50 to 100 times higher

Better predictions of efficacy and safety through greater accuracy of data collection and analysis Continuously updated database that facilitates interpretation of results by benchmarking against known compounds In certain embodiments, the present invention combines contemporary understanding of the measurement of animal behavior and the relationship of these behaviors to CNS disorders with state-of-the-art video capture and digitizing techniques and data management. The result can be fully automated, standardized system for conducting behavioral, neurological, biochemical and/or physiological experiments on mice or other laboratory animals and collecting, processing, storing and analyzing the resulting data.

The present invention also contemplates methods of conducting informatics and drug assessment businesses utilizing the apparatus, methods and databases of the present invention.

This invention provides a system for use in the assessment of behavioral characteristics that depend on different genetic backgrounds, genetic manipulations and drug effects. In one embodiment, the system comprises a module for collecting physical and biological data concerning a test subject. The module further communicates with a processor that interprets the data to capture and time-stamp the active pixels in the video input. In one embodiment the data collection hardware is replicated in large numbers allowing many subjects to be tested simultaneously. Animals observed at the same time may be part of the same experiment or a variety of different experiments. The system and method also allows hypothesis and validation of test animal behavior when the test animal is exposed to manipulation and/or an experimental drug, or when genetically manipulated animals are studied.

The apparatus and method used to assess animal behavior includes a module having one or more sensors that collectively obtain a variety of physical and biological data from a test subject. The sensors of the apparatus also may provide for the ability to simultaneously obtain data pertaining to different states in the data collecting hardware. Such states include but are not limited to the position of different mechanical parts of the hardware, active video pixels that may or may not correlate with the subjects position and movement, the signals arising from telemetric devices such as cardiac signals and any other analogical or digital signal that can be collected simultaneously (or within a close time window). Time stamped data is stored in a secondary database (where primary database refer to a putative off line storage of video images and other raw data) that allows sophisticated mining. Complex signals are summarized in probability maps using, for example, hidden Markov models (HMMs) to assign transition probabilities between different combinations of the many variables collected. Preferably low-probability states are not dropped from the model, as these low-probability states will help define the more subtle characteristics of the drug or gene signature. These probability maps will be differential, a result of the comparison between a control group and the experimental group. Multiple-dimensional modeling of the test subject based on the system's interpretation of the data allows pattern recognition of the drug signature, predictive drug analysis, and interpretation of the phenotype of a genetically engineered animal.

II. Definitions

"Accuracy" can be an important factor in assessing the success of data mining. When applied to data, accuracy refers to the rate of correct values in the data. When applied to models, accuracy refers to the degree of fit between the model and the data. This measures how error-free the model's predictions are.

The term "API" refers to an application program interface. When a software system features an API, it provides a means by which programs written outside of the system can interface with the system to perform additional functions. For example, a data mining software system of the subject invention may have an API which permits user-written programs to perform such tasks as extract data, perform additional statistical analysis, create specialized charts, generate a model, or make a prediction from a model.

An "association algorithm" creates rules that describe how often behavioral, neurological, biochemical and/or physiological events have occurred together. Such relationships are typically expressed with a confidence interval.

The term "backpropagation" refers to a training method used to calculate the weights in a neural net from the data.

The term "binning" refers to a data preparation activity that converts continuous data to discrete data by replacing a value from a continuous range with a bin identifier, where each bin represents a range of values. For example, the number of convulsion episodes per hour could be converted to bins such as 0, 1-5, 6-10 and over 10.

"Categorical data" fits into a small number of discrete categories (as opposed to continuous). Categorical data is either non-ordered (nominal) such as gender, age or weight of the animal, or ordered (ordinal) such as high, medium, or low responses to a stimuli.

The term "classification" refers to the problem of predicting the number of sets to which an item belongs by building a model based on some predictor variables. A "classification tree" is a decision tree that places categorical variables into classes.

A "clustering algorithm" finds groups of items that are similar. For example, clustering could be used to group drugs according to effect on ambulatory movements, pain sensitivity, convulsions, cardiac output and QT interval. It divides a data set so that records with similar content are in the same group, and groups are as different as possible from each other. When the categories are unspecified, this is sometimes referred to as unsupervised clustering. When the categories are specified a priori, this is sometimes referred to as supervised clustering.

The term "confidence" refers to a measure of how much more likely it is that B occurs when A has occurred. It is expressed as a percentage, with 100% meaning B always occurs if A has occurred. This can also be referred to this as the conditional probability of B given A. When used with association rules, the term confidence is observational rather than predictive.

"Continuous data" can have any value in an interval of real numbers. That is; the value does not have to be an integer. Continuous is the opposite of discrete or categorical.

The term "degree of fit" refers to a measure of how closely the model fits the training data.

The term "discriminant analysis" refers to a statistical method based on maximum likelihood for determining boundaries that separate the data into categories.

The "dependent variables" (outputs or responses) of a model are the variables predicted by the equation or rules of the model using the independent variables (inputs or predictors).

Frame: A single image from a video sequence.

Field: A portion of a video frame. Many video cameras generate interlaced video, in which each full frame is made by alternating lines from two Fields.

The term "gradient descent" refers to a method to find the minimum of a function of many variables.

The "independent variables" (inputs or predictors) of a model are the variables used in the equation or rules of the model to predict the output (dependent) variable.

The term "itemsets" refers to a set of items that occur together.

The phrase "k-nearest neighbor" refers to a classification method that classifies a point by calculating the distances between the point and points in the training data set. Then it assigns the point to the class that is most common among its k-nearest neighbors (where k is an integer).

The term "machine learning" refers to a computer algorithm used to extract useful information from a database by building probabilistic models in an automated way.

The term "mode" refers the most common value in a data set. If more than one value occurs the same number of times, the data is multi-modal.

A "model" can be descriptive or predictive. A "descriptive model" helps in understanding underlying processes or behavior. For example, an association model describes the effects of a drug on animal physiology as manifest in the tested behaviors. A "predictive model" is an equation or set of rules that makes it possible to predict an unseen or unmeasured value (the dependent variable or output) from other, known values (independent variables or input). For example, a predictive model can be used to predict side-effects of a drug in humans based on behavioral, neurological, biochemical and physiological data for the drug when used in non-human animals.

Motion Artifact: Inaccuracy in a video image due to motion in the imaged scene. Especially when significant motion occurs between the acquisition of the to fields which make up a frame.

A "node" is a decision point in a classification (i.e., decision) tree. Also, a point in a neural net that combines input from other nodes and produces an output through application of an activation function. A "leaf" is a node not further split—the terminal grouping—in a classification or decision tree.

Occlusion: In an image, the obstruction of an object or portion of the background by objects in the foreground.

A "regression tree" is a decision tree that predicts values of continuous variables.

Segmentation: The identification and labeling of those image pixels that make up an object of interest, such as a mouse, so that those pixels can be distinguished from the image background.

The term "significance" refers to a probability measure of how strongly the data support a certain result (usually of a statistical test). If the significance of a result is said to be 0.05, it means that there is only a 0.05 probability that the result could have happened by chance alone. Very low significance (less than 0.05) is usually taken as evidence that the data mining model should be accepted since events with very low probability seldom occur. So if the estimate of a parameter in a model showed a significance of 0.01 that would be evidence that the parameter must be in the model.

"Supervised learning" refers to a data analysis using a well-defined (known) dependent variable. All regression and classification techniques are supervised. In contrast, "unsupervised learning" refers to the collection of techniques where groupings of the data are defined without the use of a dependent variable. The term "test data" refers to a data set independent of the training data set, used to evaluate the estimates of the model parameters (i.e., weights).

A "time series" is a series of measurements taken at consecutive points in time. Data mining methods of the present invention that handle time series can incorporate time-related operators such as moving average. "Windowing" is used when training a model with time series data. A "window" is the period of time used for each training case.

The term "time series model" refers to a model that forecasts future values of a time series based on past values. The model form and training of the model can take into consideration the correlation between values as a function of their separation in time.

The term "training data" refers to a data set independent of the test data set, used to fine-tune the estimates of the model parameters (i.e., weights).

"Visualization" tools graphically display data to facilitate better understanding of its meaning. Graphical capabilities range from simple scatter plots to complex multi-dimensional representations. III. Data Generation and Analysis A. Behavioral Data The behavioral data can include data on one or more of sleeping, grooming, locomotion (including ambulatory and non-ambulatory movements, foot misplacement, and the like), rearing, stereotypic behavior, digging, body weight, temperature, anxiety, intake, pain sensitivity, convulsions, cardiac response (e.g., output, QT interval), respiration (e.g., rate, $O_2$ or $CO_2$), learning, memory (short/long), task switching, attention, discrimination, motivation, response inhibition, reward sensitivity, avoidance, startle, tolerance and withdrawal.

In certain embodiments, the behavioral data includes data representative of one or more of immobility, approach, circling, chewing, digging/burying, drinking, eating, freezing, gait (normal, abnormal), grooming (face, anogenital, abnormal), huddling, intake, jump (horizontal, vertical, stereotyped), lever-pressing, locomotion (walk, run), nose-poking, rearing (normal, stereotyped), seizures (tonic, clonic), self-biting, scratching (normal, stereotyped), stretch-attend, sleeping, sniffing, startle, stereotypic behavior, tail position, temperature, twitching, yawning.

The behavioral data may also, or alternatively, include data concerning anxiety, attention, arousal, avoidance, circadian rhythms, discrimination, habituation, learning, memory, motivation, pain sensitivity, response inhibition and sensitization, reward sensitivity, sensitization, sensory motor gating, sleeping patterns, stereotypic behavior, task switching, tolerance, withdrawal, fear conditioning, home cage observation, Irwin/neurological effects, light/dark box, locomotor activity (open field test), prepulse inhibition of startle—startle habituation, pain response, metabolic chambers, and operant conditioning.

Merely for illustration, the ability of the subject system to capture some of the behavioral states mentioned above in a fully automated way is briefly described below in greater detail with respect to a mouse (an ideal test animal) although it will be readily appreciated that the instant invention is not limited to just this species of animal.

High Tower Walk Test: From all measures mentioned misstepping in between rods systematically arranged on a surface seems to provide high sensitivity to the sedative and ataxic effects of some drugs.

Orienting Movement: In this test the latency to orient to a tactile stimulus (air puff directed to right or left side of head) provides sensitivity to moderate to severe dopaminergic depletion in animals treated with particular drugs.

Locomotor Activity: Apart from monitoring spontaneous activity and response to acute drug effects, changes in locomotor activity over repeated injections may reflect tolerance and sensitization to drug effects. Sensitization to amphetamine, for example, is reflected with an increased response to the hyperlocomotor effects of the drug upon repeated exposure.

Circadian Activity: Measurement of general activity in a day-night cycle. Sensitive to hypothalamic dysfunction as well as neuromuscular damage. These data can be combined with measures of food and water consumption over the circadian cycle to assess eating, spontaneous circadian behavior or non-specific drug effects. Although this is a test that has been successfully automatized (using lickometers, running wheels, etc), the instant invention will provide comprehensive assessment of all ongoing behaviors.

Pre-pulse Inhibition: A test of the ability of animals to "gate" or inhibit the effect of environmental information. Normal animals exhibit less of a startle response to a sudden loud sound if it has been preceded by a softer sound. Its impairment may typify some aspects of schizophrenia. A simple addition to the subject system (e.g., for delivery of localized brief air puff) will enable this capability.

Defensive Burying Test: In this test the mouse is challenged with a mild electric shock upon contact with a shock probe. Preliminary studies show that the fear responses (approach to the probe, contact, burying, freezing) of mice in this test are sensitive to anxiolytic and antidepressant treatment.

(i) Overt Behavior

Motor responses typically include changes in movement or motor function, or lack thereof. Several aspects of motor function can be assessed: frequency of occurrence, type, degree of motor coordination, temporal pattern and functional significance. These different aspects can be assessed in different ways. For example, motor responses may be examined by requiring a response consisting of moving a lever, pecking a key or moving an object. Additionally, motor responses may be more extensively characterized by forcing the test subject to perform in somewhat extreme conditions with the use of some physical challenge such as an obstacle course or maze. Many obstacles can be incorporated into the invention including stairs, treadmills, and the like.

Motor activity, as defined in this description, is meant to be any physical activity such as a physical change or any movement or lack of by the test subject. For example, such activity may include, but is not limited to immobility, approach, circling, chewing, digging/burying, drinking, eating, freezing, gait (normal, abnormal), grooming (face, anogenital, abnormal), huddling, intake, jump (horizontal, vertical, stereotyped), lever-pressing, locomotion (walk, run), nose-poking, rearing (normal, stereotyped), seizures (tonic, clonic), self-biting, scratching (normal, stereotyped), stretch-attend, sleeping, sniffing, startle, stereotypic behavior, tail position, temperature, twitching, yawning.

Other biological changes may include responses associated with a change in the functioning of the nervous system and may include, for example, changes in heart rate, blood pressure, temperature, perspiration, piloerection, and respiration. In one possible embodiment of this invention measurement of heart rate (through telemetry or another technique) and other physiological measures are recorded in parallel with the behavioral data. Another form of biological response which may be used to contribute to defining an animal behavior according to this invention is a change in neuronal activity measured using a variety of means known to those skilled in the art including, for example, the use of chronically implanted electrodes to measure neuronal activity.

Conditioned responses may also be studied by the invention including, but not limited to, the effects of drugs on a test subject prior to and/or after behavioral conditioning.

By measuring a plurality of responses this invention provides a means for objectively monitoring and detecting changes in animal behaviors. Complex behaviors such as aggression, emotional responses to aversive stimulation, nursing and other maternal behaviors, and the like may thus be assessed according to this invention by monitoring a plurality of responses occurring when such behaviors are exhibited, and by using sophisticated data mining tools as described below. Effects of drugs on the animal's behaviors may then be determined by detecting changes in the plurality of behavioral and physiological measures captured by this invention.

(ii) Additional Aspects of Behavior

This invention serves to capture unconditioned and conditioned behavior in parallel with physiological data. Unconditioned behavior may be assessed by the invention for use in the research on the effects of drugs. This type of behavior is elicited by specific stimuli and usually involves no specific training or conditioning to the test subject. Responses are typically part of the behavioral repertoire of the species and are expressed under suitable environmental conditions. Although factors responsible for the occurrence of these behaviors presumably lie in the organism's distant evolutionary past, certain unconditioned responses, called reflexes, can be brought under more direct and immediate experimental control through the use of various procedures known to those skilled in the art. Such procedures consist of expanding the range of stimuli capable of producing or eliciting a response and by exploring the pattern of responses elicited by specific types of stimuli or arrangement of stimuli. For instance, considerable use has been made of a procedure for the study of antipsychotic drugs in which a strong tactile or auditory stimulus is presented and a "startle" response is elicited. When the startle reflex is reduced by the presentation of a brief stimulus presented immediately before the eliciting startle stimulus, "prepulse inhibition" results. This phenomenon has been useful in the evaluation of neuroleptic drugs and other such drugs. In one embodiment of this invention such a phenomenon will be evaluated.

With the use of conditioned responses (Pavlovian and/or operant) memory and learning can be assessed. The invention may also be used for the study of drugs that impair or enhance memory, and by gene manipulations that result in enhanced or impaired learning and memory.

Pavlovian conditioning can be obtained by training the test subject to expect that a reinforcement will be delivered, for example, after a given period after an auditory or visual signal is presented. Behavior and physiological responses in anticipation and in response to the stimulus can then be registered and compared against a control group. Operant conditioning can be studied by the invention by training the test subject to perform a response to obtain reward or to avoid punishment. In this realm, a further embodiment of the invention is control of inputs (lever, nose poke, etc) and outputs (lights, sounds, etc) that may serve to enforce schedules of reinforcement.

The invention can also be used to study complex species-specific behavior patterns in animals. These types of behaviors have evolved in situations of survival. Selection pressure has resulted in the development of sensory and motor functions, sexual behavior, care of the young, social cohesion and dispersion, and interactions with other species in the ecological niche. These elaborate behavior patterns are the result of phylogenetic and ontogenetic processes. Typically, no explicit conditioning is required for their expression, although they can be modified. For example, it is possible to reproduce under controlled conditions the essential features of situations promoting the display of those elements of the behavioral repertoire that are characteristic of exploration, foraging, reproduction, maternal care, attachment to and separation from the group, as well as aggression and defense.

The invention may, depending on the implementation, use another method in the experimental analysis of behavior known as stimulus discrimination. In essence, this procedure consists of establishing a drug as a stimulus in the presence of which a particular response is reinforced. The use of a drug to gain discriminative control over behavior is very different from that mentioned earlier in which a drug elicits a reflexive-like behavior. When a drug develops properties of a discriminative stimulus, it "sets the occasion" for a response. This phrase means that the administration of the drug does not merely produce the response but makes the response more likely to occur because of past consequences in the presence of that stimulus.

Typically, when a drug is established as a discriminative stimulus, a single dose of a drug is selected and, following its administration, one of two responses are reinforced. For example, with rodents or nonhuman primates this consists of pressing one of two simultaneously available levers for reinforcement after a fixed number of correct responses. Alternatively, when saline or a control vehicle is administered, responses on the other operant are reinforced. Over a number of experimental sessions, a discrimination develops between the internal cues induced by the drug and by the control substance, with these interoceptive stimuli produced by the two solutions seen as "guiding" or controlling behavior in much the same manner as any external stimulus such as a visual or auditory stimulus. Once established, it is possible to perform several additional studies to investigate aspects of the drug stimulus in the same way as one might investigate other physical stimuli. Thus, it is possible to determine "intensity" gradients or dose-effect functions as well as generalization functions that are directed towards determining how similar the training drug dose is to a different dose or to another drug that is substituted for the training stimulus. It is also possible to use drug discrimination techniques as a means for exploring changes in neurotransmitter function following exposure to neurotoxins or other types of interventions that may alter receptors in the central nervous system.

Protocols for eliciting conditioned and unconditioned responses may be automated, and done by the invention. For example, measurements of behavior in unconditioned and conditioned tests such as startle in response to a loud stimulus, or an avoidance response to a nociceptive stimulus will result in precise and accurate data through the use of the invention because of the automated and thorough data capturing capabilities of the device.

(iii) Objectivity in the Measurement of Behavior

Adequate measurements of the behavioral expressions of affect, for example, require familiarity with the species-specific behavior in order to avoid impressionistic and anthropomorphic accounts that can lead to a misinterpretation by the observer. The invention avoids such a bias by providing a complete analysis of the test subject's behavior objectively through pre-programmed logic to determine the behavior from the behavioral and physiological responses. Quantitative ethological methods can be used in the invention's comprehensive analyses by incorporating the traditional behavioral measurements of latency, frequency, and duration parameters, as well as a quantification of the temporal and sequential pattern. Increasingly more sophisticated levels of analysis can be performed by the invention to assess not just the presence or absence of these behaviors, but also whether or not the species-typical acts, postures, displays, and gestures are performed in a particular temporal topography of intensity and frequency.

The invention will provide precise analyses of salient and subtle elements in an animal's repertoire for detecting behaviorally selective drug action. For example, a broad profile of action for a desired drug effect can be assessed, to cover central and side effects. As the availability of agents to treat various neurological and psychiatric disorders increases, and the selectivity of the drugs available to treat those disorders improves, it will be possible to use this information to design even more sensitive and selective procedures for the evaluation of pharmacological activity. Thus, the invention can further drug research.

(iv) Other Morphological and Physiological Tests a. Radiotelemetry Recording

Information on physiological parameters of mice such as heart rate, blood pressure and body temperature can be critical in evaluating effects of genetic manipulations and drug treatments on the brain and the body of the animal. The state-of-the-art technology to address these issues is continuous, long-term monitoring of these parameters by using radiotelemetry recording. This can be accomplished by implanting a small device into the body of the animal that transmits signals registered by a computer for an extended period of time, up to several months without disturbing the mouse or its environment. Changes in heart rate, blood pressure or body temperature can provide important information to understand gene function and drug effects.

This approach can be utilized for mutant mouse phenotyping, and to pick up efficacy or side-effects of novel compounds. Furthermore, radiotelemetric recording can extend and complement the behavioral signature analysis with physiological signatures to obtain a full profile.

b. In Vivo Microdialysis in the Brain

Changes in the level of neurotransmitters, and therefore, information processing in the brain, have been described as a principal mechanism that underlies normal and pathological behavior. This can be monitored by implanting a small dialysis probe into the brain nuclei of interest then measuring the concentrations of neurotransmitters that have been implicated in CNS disorders, in awake, freely moving mice. In certain embodiments, in vivo microdialysis measurement of major neurotransmitters and their metabolites can be carried out, e.g., on mutant mice and on mice treated with drugs. This allows the determination and correlation of quantitative changes in neurochemistry and behavior on the same subject at the same time.

c. Functional Neuromorphology

Based on the understanding of the relationship between genes, brain structures and function, a comprehensive range of functional neuromorphology services designed to assess changes in a gene and/or protein expression, structural changes, cell death and cell birth can be carried out.

d. In Situ Hybridization Histochemistry

The subject method can also include the use of high-quality, quantitative (radioactive) and semi-quantitative (fluorescent) in situ hybridization histochemistry aided by mathematical tools to measure changes in gene expression in the brain of mutant mice as models of CNS disorders or in response to drug treatment. For instance, high-resolution, non-radioactive fluorescent in situ hybridization histochemistry can be used to identify expression of multiple genes at a single-cell level that can be combined with immunohistochemistry to visualize proteins expressed in the same cells. The combination of quantitative radioactive and high-resolution, non-radioactive in situ hybridization technologies allows acquisition of information on quantitative changes of gene expression in the mouse brain at the level of a single neuron within a particular brain nucleus.

e. Neurohistology

Histology can be used to characterize gross morphological changes such as lesions and neurodegeneration, or to measure structure volume, cell count, etc. For example, cell loss and volume reduction in the hippocampus is characteristic of depression and aging, and is observed in certain respective animal models. In certain embodiments, the subject method also measures structural changes including dendritic and spine morphology, cell death and neurogenesis in the adult brain.

f. Immunohistochemistry

Immunohistochemistry can be used for neurochemical cell phenotyping; localization of neurons containing certain peptides, enzymes or receptors; and measurement of synaptic markers. Immunohistochemistry can also be used to measure neuronal activity by measuring, for example the expression of the immediate-early gene product protein, cFos.

g. Microdissection

Microdissection of the animal brain, e.g., using the "punch method" or the like, can provide anatomical identification of brain nuclei suitable for gene expression profiling to determine response to drugs, behavioral intervention and genetic manipulation.

h. Microinjection Technology

Microinjection technology can be used to target the cerebral ventricles as well as identified brain nuclei in a test animal. This can be used in preparing antisense and viral vector treated mice and for compound/peptide delivery where penetration is poor.

i. Standard Histological Staining Procedures

Standard histology can be used to characterize gross morphological changes such as lesions, neurodegeneration, or to measure structure volume, cell counts, etc. For example, cell loss and volume reduction in the hippocampus is characteristic of depression and aging, and is also observed in certain respective animal models.

j. Golgi Staining

Golgi staining can be used to visualize dendritic trees and spines of neurons in the brain. Dendritic length and spine density can be measured from individual, Golgi stained neurons. Dendritic morphology and spine density has been shown to be altered in animal models of depression and in the cortex and hippocampus of schizophrenics. Changes in spine density may reflect changes in number of synaptic connections and therefore altered activity of the neural network.

k. Neuroplasticity Studies

Neuronal death by apoptosis and necrosis, and cell proliferation in the adult mouse brain, can be measured by TUNEL staining, silver staining, and BrdU labeling, respectively. Rate of neurogenesis can be determined by measuring BrdU-positive cells double-labeled with neuronal markers using confocal fluorescent microscopy. Neuronal death and neurogenesis can be influenced by genes, various treatment conditions or experimental manipulations.

l. Genotyping

PCR or Southern-blot based genotyping procedures and the like can be used to identify and breed client owned transgenic or knock-out mice housed in the service provides colonies for the purpose of behavioral testing.

B. Database Analysis Techniques

Various data mining techniques can be used as part of the subject invention. In certain preferred embodiments, the data mining system uses classification techniques, such as clustering algorithms, which find rules that partition the database into finite, disjoint, and previously known (or unknown) classes. In other embodiments, the data mining system uses association techniques, e.g., of summarization algorithms, which find the set of most commonly occurring groupings of items. Yet in other embodiments, the datamining system uses overlapping classes.

In one embodiment, the subject method using a data mining technique based on association rules algorithms. These techniques derive a set of association rules of the form X→Y, where X and Y are sets of behavioral, neurological, biochemical and physiological responses and each drug administration is a set of literals. The data mining task for association rules can be broken into two steps. The first step consists of finding all large itemsets. The second step consists of forming implication rules with a user specified confidence among the large itemsets found in the first step. For example, from a behavioral dataset, one may find that an association rule such as drugs which caused a reduced sensitivity to pain often cause a decrease in respiratory rate. Association rules can also be more complex, requiring that two or more criteria are met in order for the rule to be evoked. A rule X→Y holds in the data set D with confidence c if c % of the occurrences of X in the data set also contain Y. The rule X→Y has support s in the data set ifs % of the entries in D contain X→Y. Confidence is a measure of the strength of implication and support indicates the frequencies of occurring patterns in the rule.

Another technique that can be used in the methods of the present invention is the process of data classification. Classification is the process of finding common properties among a set of "objects" in a database, and grouping them into various classes based on a classification scheme. Classification models are first trained on a training data set which is representative of the real data set. The training data is used to evolve classification rules for each class such that they best capture the features and traits of each class. Rules evolved on the training data are applied to the main database and data is partitioned into classes based on the rules. Classification rules can be modified as new data is added.

Yet another data mining technique that can be used in the subject method is the use of sequential pattern mining. This technique can be used to find sequential patterns which occur a significant number of times in the database. This analysis can be used to detect temporal patterns, such as the manifestation of secondary adaptation or effects involving combinatorial therapies. Time-Series clustering is another data mining technique that can be used to detect similarities in different time series.

In yet another embodiment, the subject method uses a clustering method for finding correlations in the behavioral database(s). In general, clustering methods can be broadly classified into partitional and hierarchical methods.

Partitional clustering attempts to determine k partitions that optimize a certain criterion function. The square-error criterion is a good measure of the within-cluster variation across all the partitions. The objective is to find k partitions that minimize the square-error. Thus, square-error clustering tries to make the k clusters as compact and separated as possible, and works well when clusters are compact clouds that are rather well separated from one another.

Hierarchical clustering is a sequence of partitions in which each partition is nested into the next partition in the sequence. An agglomerative method for hierarchical clustering starts with the disjoint set of clusters, which places each input data point in an individual cluster. Pairs of clusters are then successively merged until the number of clusters reduces to k. At each step, the pair of clusters merged are the ones between which the distance is the minimum. There are several measures used to determine distances between clusters. For example, pairs of clusters whose centroids or means are the closest are merged in a method using the mean as the distance measure ($d_{mean}$). This method is referred to as the centroid approach. In a method utilizing the minimum distance as the distance measure, the pair of clusters that are merged are the ones containing the closest pair of points ($d_{min}$). This method is referred to as the all-points approach.

In another embodiment, the subject method uses Principal Component Analysis (PCA). This is not a classification method per se. The purpose of PCA is to represent the variation in a data set into a more manageable form by recognizing classes or groups. The assumption in PCA is that the input is very high dimensional (tens or even thousands of variables). PCA extracts a smaller number of variables that cover most of the variability in the input variables. As an example, suppose there are data along a line in 3-space. Normally one would use 3 variables to specify the coordinates of each data point. In fact, just 1 variable is needed: the position of the data point along the line that all the data lies on. PCA is a method for finding these reductions. An advantage to PCA is that it can be a reasonably efficient method whose reduction is well founded in terms of maximizing the amount of data variability explained with use of a smaller number of variables.

Still another embodiment utilizes a neural net or neural network, e.g., a complex non-linear function with many parameters that maps inputs to outputs. Such algorithms may use gradient descent on the number of classification errors made, i.e. a routine is implemented such that the number of errors made decreases monotonically with the number of iterations. Gradient descent is used to adjust the parameters such that they classify better. An advantage to neural nets is that such algorithms can handle high dimensional, non-linear, noisy data well.

The neural net can be trained with "supervision", i.e., a mechanism by which the net is given feedback by classifying its responses as "correct" or "incorrect". It eventually homes into the correct output for each given input, at least with some probability. Such machine learning techniques may be advantageously employed for either or both of vision classification components or data mining components of the instant invention.

Supervised learning requires the buildup of a library of readily classified data sets for input into the neural net. Although more economic in terms of the amount of data needed, supervised learning implies that only pre-determined classes can be ascribed to unseen data. To allow for the possibility of finding a novel therapeutic class, such as "anti-depressant drugs with anti-manic component" unsupervised clustering could be more appropriate.

In certain embodiments, a preferred method can combine both types of learning: a supervised learning of the neural net until it correctly classifies a basic training set but which also utilizes unsupervised learning to further subdivide the trained classes into meaningful sub-classes, or to add completely new sub-classes.

Principal component analysis (PCA) involves a mathematical procedure that transforms a number of (possibly) correlated variables into a (smaller) number of uncorrelated variables called principal components. The first principal component accounts for as much of the variability in the data as possible, and each successive component accounts for as much of the remaining variability as possible. Traditionally, principal component analysis is performed on a square symmetric matrix of type SSCP (pure sums of squares and cross products), Covariance (scaled sums of squares and cross products), or, Correlation (sums of squares and cross products from standardized data). The analysis results for matrices of type SSCP and Covariance do not differ. A Correlation object is preferably used if the variances of individual variates differ much, or the units of measurement of the individual datapoints differ, such as is the case when the analysis comprises data from behavioral, neurological, biochemical and physiological measures. The result of a principal component analysis on such objects will be a new object of type PCA.

In still other embodiments, the subject method utilizes K-means and fuzzy clustering. Gaussian mixture models are a common version of this. These techniques are "unsupervised" clustering methods. They assume the user has no outputs, but would like to group the data anyway according to inputs that are similar to each other. The idea is to choose a model for each cluster. For example, each cluster may consist of points inside a hyper-sphere centered at some location in the input space. These methods automatically determine the number of clusters, place them in the correct places, and determine which points belong to which clusters. An advantage to these techniques is that they can be efficient algorithms and can do a good job of finding clusters. This is a method of choice when the user does not have a priori information about the classes Another embodiment utilizes the hierarchical clustering Serial Linkage Method. This is an unsupervised clustering method in the same sense as K-means and fuzzy clustering. Here individual points are joined to each other by being close to each other in the input space. As these points are joined together, they define clusters. As the algorithm continues, the clusters are joined together to form larger clusters. Compared to K-means and fuzzy clustering, hierarchical clustering has the advantage that clusters can have arbitrary non-predefined shapes and the result correctly shows "clusters of clusters." A disadvantage to these methods is they tend to be more sensitive to noise.

Yet another embodiment utilizes a nearest neighbor algorithm. This is a true supervised learning method. There is a set of training data (inputs, i.e. datapoints, and outputs, i.e. classes) that are given in advance and just stored. When a new query arrives, the training data is searched to find the single data point whose inputs are nearest to the query inputs. Then the output for that training data point is reported as the predicted output for the query. To reduce sensitivity to noise, it is common to use "k" nearest neighbors and take a vote from all their outputs in order to make the prediction.

In yet another embodiment, the subject method uses a logistic regression algorithm. This is related to linear regression (fitting a line to data), except that the output is a class rather than a continuous variable. An advantage is that this method provides a statistically principled approach that handles noise well.

Still another embodiment utilizes a Support Vector Machine algorithm. This also has a linear separator between classes, but explicitly searches for the linear separator that creates the most space between the classes. Such techniques work well in high dimensions. Yet another embodiment relies on a Bayes Classifier algorithm. The simplest form is a naive Bayes classifier. These algorithms build a probabilistic model of the data from each class. Unsupervised methods above may be used to do so. Then, based on a query, the model for each class is used to calculate the probability that that class would generate the query data. Based on those responses, the most likely class is chosen.

Yet another embodiment utilizes a Kohonen self organizing maps (SOM) Clustering algorithm. These algorithms are related to neural nets in the sense that gradient descent is used to tune a large number of parameters. The advantages and disadvantages are similar to those of neural networks. In relation to neural networks, Kohonen SOM clustering algorithms can have the advantage that parameters can be more easily interpreted, though such algorithms may not scale up to high dimensions as well as neural nets can.

The subject databases can include extrinsically obtained data, such as known protein interactions of a drug, chemical structure, Kd values, Pk/Pd parameters, IC50 values, ED50 values, TD50 values and the like.

The system of the present invention can also provide tools for visualizing trends in the dataset, e.g., for orienting, to simplify user interface and recognition of significant correlations.

Certain embodiments of the subject system are designed to have increased power to capture most aspects of behavior that are measured in standard behavioral tests, and other more subtle aspects of behavior that may add meaning to a signature. Being able to record behavior and physiology with a sampling rate of, e.g., 30 times a second or more brings enormous statistical power to define robust signatures.

Working with drug signatures implies that standard statistical tests are no longer the best means to analyze the data for several reasons. The first is that separately analyzing dependent measures defeats the purpose of gathering data in parallel and ignores the potential of analyzing signatures as a whole. Second, assessing more that one dependent measure per experiment inflates the probability of a Type I error the chance of finding a false positive, if the sample size is kept constant. Taking into consideration the whole collection of data points that constitute a signature solves these problems at once.

Example 1

Analysis

The output of the subject system can be visualized as a stream of numbers (also called "time series") representing the parameters that result from the computer vision algorithm, and those that arise from the other measuring devices implemented in the subject system (e.g., cages).

Figures 11A, 11B, 11C:
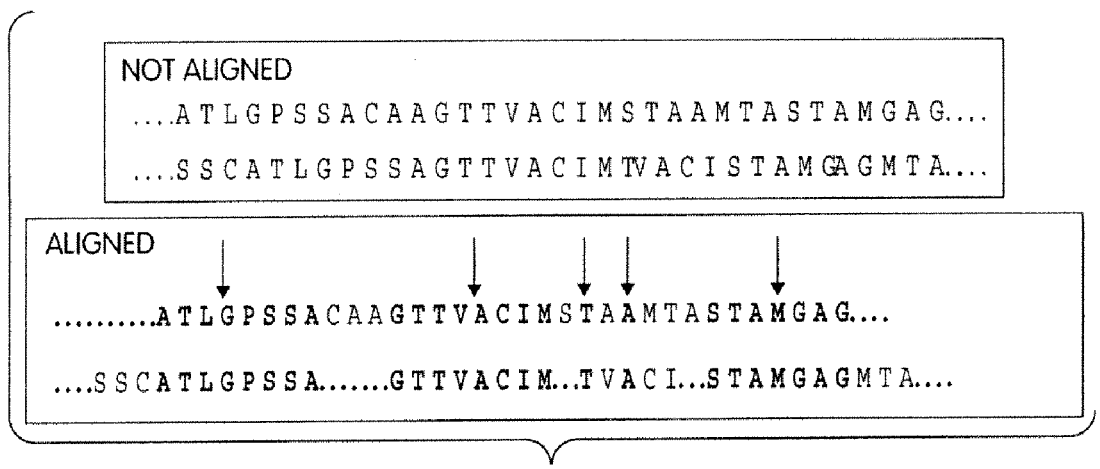
FIGS. 11A and 11B show an exemplary combination of data streaming from an animal in an embodiment of the subject system.
FIG. 11C shows two different sequences of behavior, obtained from two different animals.

FIG. 11A shows an exemplary combination of data streaming from an animal in an embodiment of the subject system. For each window (in this case shown to coincide with the ECG sliding window) a given set of states and parameters is obtained from each mouse. These dynamically changing "frames" of behavior present different types of complexity. First, they change over time in what is normally called the "time course" of behavior (e.g., rearing may be very frequent initially but decline significantly towards the end of the session). Second, each frame has some dependency on the previous one (e.g., an animal cannot step down if it has not stepped up first), and this is called the "temporal structure" of behavior. Whereas the first problem can be addressed using time-series analysis, as discussed below, the second can be analyzed by providing snapshots of behavior that capture the temporal structure of behavior.

It must be noted that the standard analyses of behavior in behavioral pharmacology do not address the issue of temporal structure, although they do address the time course of behavior.

To further illustrate, a possible way to summarize time series data in preparation for statistical analysis first reduces the problem of having several parallel streams of data to a unique simple sequence of three behaviors: grooming, running and locomotion.

FIG. 11B recapitulates the sequence presented in FIG. 11A, though letters are added each coding to signify that each combination of variables in each frame has been identified as a distinct state (by the learning algorithm). One can now think of a single stream of states (no longer just behavioral, as now we have succeeded to integrate physiology and behavior).

FIG. 11C shows two different sequences of behavior, obtained from two different animals. In certain embodiments, it will be desirable to find the similarity between the two sequences. FIG. 11C shows a way to align the sequences utilizing string matching algorithms, such as those used in the BLAST algorithm or AGREP algorithms.

The principle can be simple: two sequences that align perfectly receive a maximum score. If there is a mismatch (in FIG. 11C the first sequence needed to be shifted 3 frames to find the first match "A T L G P S S A"). For each shift needed to improve matching, a value is subtracted from the maximum score. As there are different ways to (imperfectly) align sequences, the best matching is the one that provides the higher score.

Figure 12:
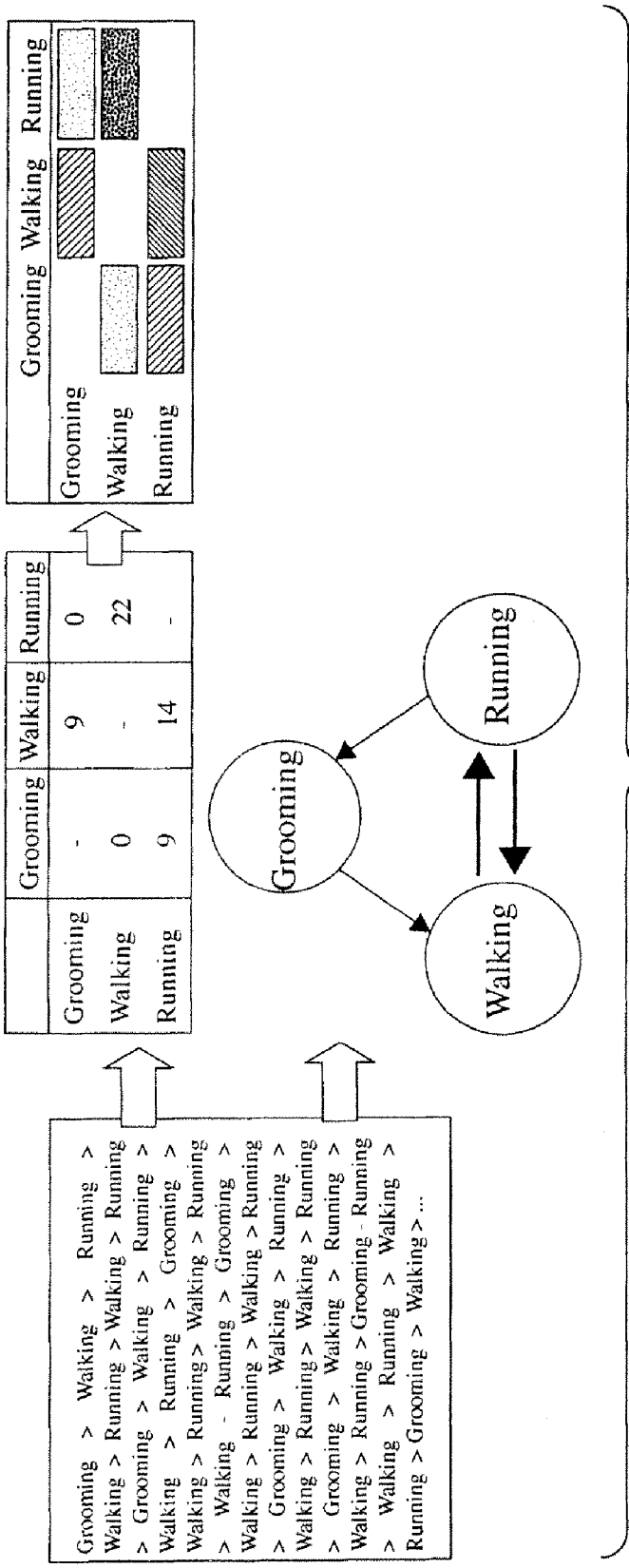
FIG. 12 shows a possible sequence of these three behaviors arising from one animal.

FIG. 12 shows a possible sequence of these three behaviors arising from one animal. The idea that a temporal structure underlies such a sequence, as mentioned before, means that states are not independent from each other, and therefore the probability that one state will occur depends on the probability that the previous state has occurred. The number of times grooming followed walking reflects such probability (plus the total frequency of grooming). Therefore, if the system counts the number of walking-grooming transitions, it will be capturing two aspects of behavior, first, how much grooming occurs (where the total frequency of grooming will be the sum of all transitions that end up in grooming, in this example walking-grooming and running-grooming) and which other state predicts grooming.

In FIG. 12, the illustrated example counted the different transitions and wrote the results on a table, a transition table or matrix. One could also represent the transitions as a diagram with more frequent transitions being represented by thicker arrows, and states as nodes (circles in the figure). This is the typical way sequences of states that are interdependent (Markov chains) are represented. This way of visualizing the transition matrices has an immediate appeal: one can see now that the animal shuttled most of the time between walking and running, and only occasionally sustained bouts of grooming, in an unidirectional loop. Although all this information was embedded in the initial sequence, no human brain could have captured these characteristics of interdependency.

To make the representation of transition matrices easier to visualize, FIG. 12 also shows a matrix in which numbers have been replaced by shades of gray, just as it is done in gene-expression analysis. In fact, the similarity with tools used in functional genomics will become apparent in the next few paragraphs.

In certain embodiments, it will be desirable to distinguish between the average drug signature for drugs of different therapeutic indications. Merely to illustrate, in such embodiments one or more of the following criteria may be important to data acquisition and/or processing:

Replication. Preferably the signature of a drug is stable and replicable, when testing is done in similar conditions.

Significance. The signature of the drug should be observed well over chance levels.

Discrimination. The signature of a drug is preferably significantly different from another drug signature, when the two drugs have no therapeutic overlap.

Testing drugs several times and comparing the results can address replication. Significance is illustrated in FIG. 13, where exemplary data is shown from an experiment in which mice were treated with one of the indicated drugs and ensuing behavior was recorded and later coded by human observers.

In the analysis of transition matrices, the average matrix of the drug treated mice was combined with the average matrix of the control mice. The control data was treated as the "population" data as it was expected to have very large numbers from mice treated with same vehicle as more and more experiments that require such vehicle are conducted.

Even though vehicle treatments may be included with the corresponding drug treated group, it may be possible to analyze control groups across experiments and build a normative vehicle dataset.

Referring again to FIG. 13, the average transition matrix was transformed as a z-score matrix based on the mean and standard error of the control matrix. In doing so, every drug transition ($f_{d,i}$) subtracted the corresponding control transition ($f_{c,i}$) and divided by the standard error ($s_{c,i}$), as in $z_{d,i} = ((f_{d,i})-(f_{c,i}))/(s_{c,i})$ was obtained. Although this is just one possible way to normalize the data (e.g., student t-scores can also be calculated), it has some intuitive appeal, as the z-scores can now be read as distance from the control in standard-deviation units. Thus, in FIG. 13, the first cell of the matrix corresponding to chlordiazepoxide (CDP), can be read as "CDP increased the number of rear-rear transitions more than 30 fold".

Normalizing data using the controls can be of importance since it may allow one to compare seemingly disparate experiments, such as behavioral drug effects in two different strains that have a different activity baseline. In other words, one can be concerned about being able to extract how much more or less of a particular behavior is observed in the treatment group as compared to the control group.

In the illustrated example, having calculated z-scores and making some assumptions about the data (e.g., a normal distribution), one can now easily visualize which of the transitions was increased or decreased significantly by the drug treatment. In FIG. 13, black and dark grays show z-scores that are significant at the 5% and 10% levels ($z<-1.96$ and $-1.96 \leq z<-1.64$, respectively) representing transitions that were significantly decreased by the drug treatment. Conversely, white and light gray show significant increases ($z>1.96$ and $z>1.64$, respectively).

Figure 9:
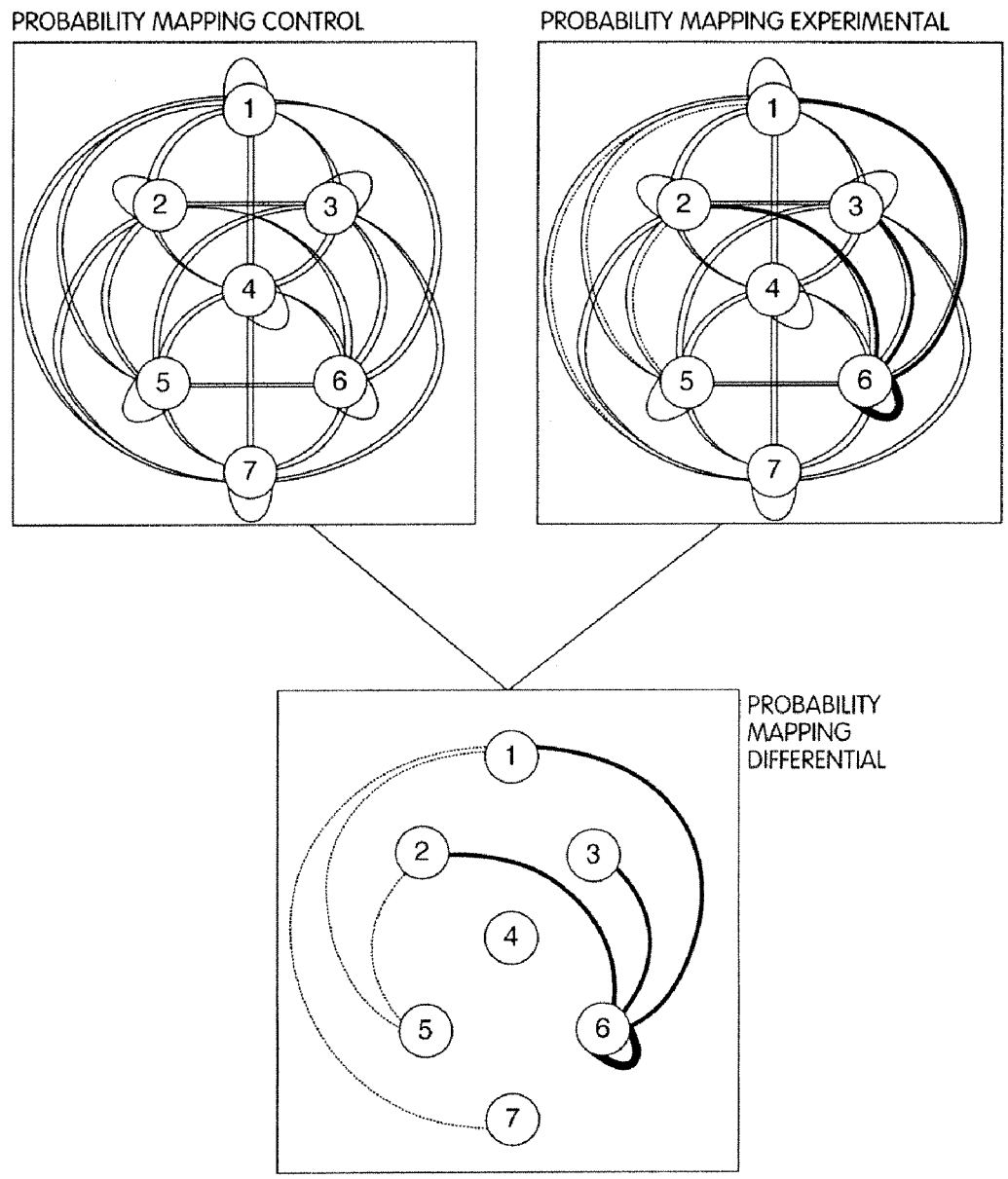
FIG. 9 is an example showing a comparison between two probability diagrams corresponding to a control and an experimental subject.

FIG. 9 shows theoretical data to illustrate the normalization procedure in a transition map form. One can think of the process of identification of a signature as a process through which all transitions that have been not affected are discarded. In FIG. 9, then, only the thicker and thinner transition lines in the experimental group are left as part of the signature, which we call "differential" to point out that the profile is based on a comparison against the control. Thus the drug signature in FIG. 9 consists of increased transitions 2-6, 3-6, and 1-6, and decreased transitions 1-7, 2-7, and 1-5, where the numbers represent behavioral, neurological, biochemical and/or physiological states.

In FIG. 13, having normalized the transition matrix for CDP and CPMC, one can now compare the significant effects of the two drugs. One might expect these drugs to differ in many respects, as CDP is an anxiolytic and CPMC an anxiogenic drug. Indeed, some of the transitions are significantly affected in opposite directions. For example, the transitions in which rearing was followed by rearing, directed burying, grooming and immobility were increased by CDP, but were decreased by CPMC.

In the case of CDP one could summarize the rear-x transition (where x is any behavior) increases by stating that rearing was increased overall, independently of what preceded it or followed it. However, although CPMC seems to decrease rearing in general, the transition analysis revealed that the effect was more specific than that, proving that transitions can reveal a lot more about behavior than simple total frequencies.

Figure 10:
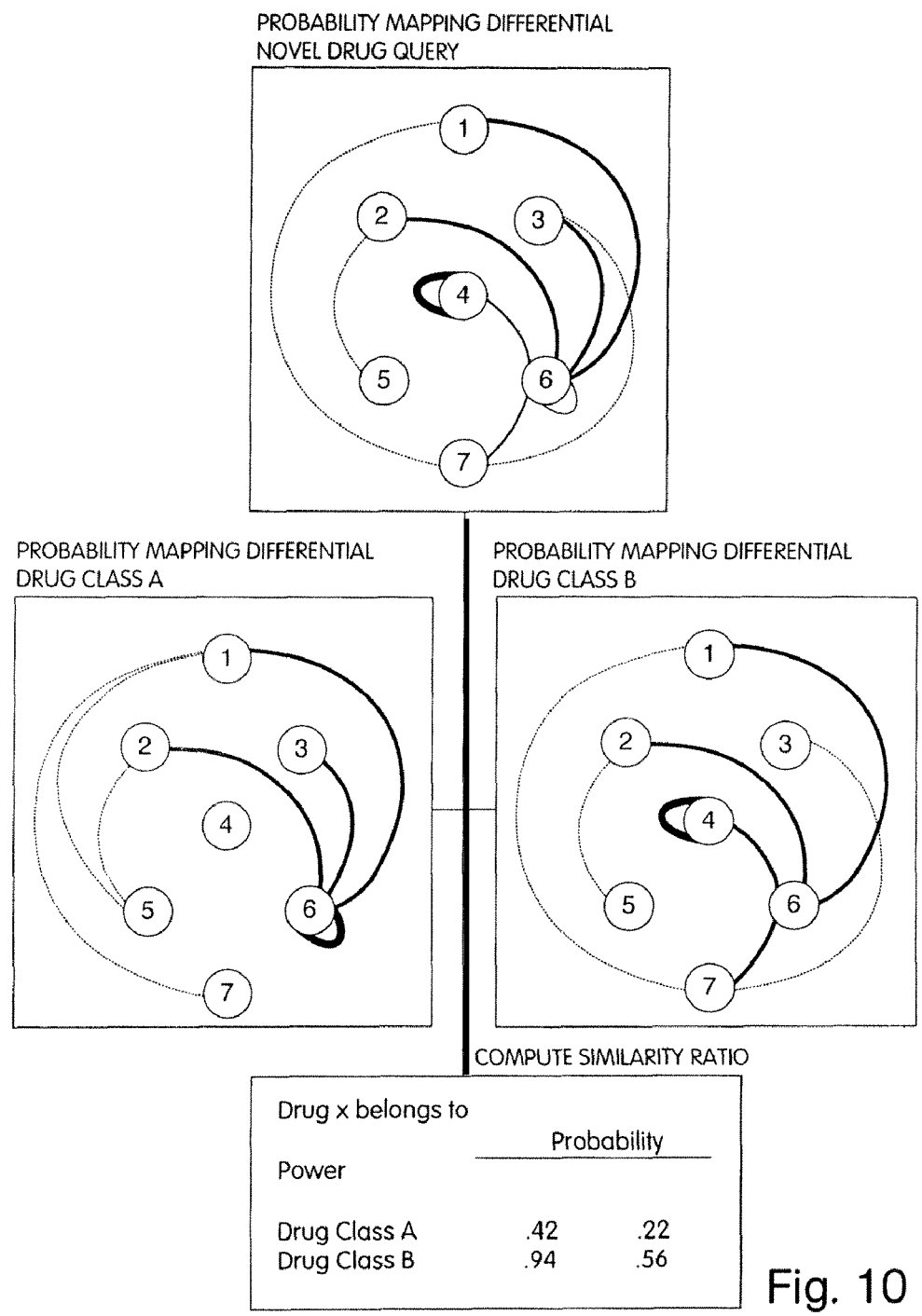
FIG. 10 is an example showing two classes of drugs resulting from the clustering analysis based on the probability diagrams, and an example showing a query of the database that results in the "diagnosis" of the new drug x, based on the normative clustering of the database.

FIG. 10 shows an exemplary process of comparison of signatures. A novel drug signature found by running a drug through the subject system is compared against the whole collection of signatures available in a database. One way one could quantify the similarities between the signatures is to compute a Chi Square, a test designed to assess differences between matrices.

Although some of the matrices dealt with in the subject system may violate some of the assumptions of this test, it will not be difficult to develop appropriate, comparable statistical tests. The Chi Square (or custom designed test) will give back a probability that the two matrices being compared are different due to chance or to the experimental treatment. This probability of "belonging" to a class can be approximated by the probability of these two signatures not being different, which is the inverse of the "p-value", or 1-p. One can also assess the power of such classification by 1-$\beta$ (probability of not missing a true difference).

The task of assigning new signatures to classes can conveniently be expressed as a pattern classification problem, and can be implemented using a component classifier based on Gaussian mixture models. This type of classifier works by considering each class independently, and fitting a parametric probability density to the corresponding distribution of signatures. As new compounds are evaluated, these distributions are used to estimate the probability that the test compound is included in each class.

New studies with known drugs can provide information that will be used to update component models and prior distributions, leading to more accurate classification in subsequent runs.

FIG. 10 shows a probability estimates, for each drug class, for an exemplary embodiment in which the probability of belonging to the class and a probability that such classification is correct. Because drugs may have more than one therapeutic indication, this example incorporates non-exclusive classes or clustering.

Further understanding of these analysis techniques may be had by reference to references as Tom Mitchell, "Machine Learning", McGraw-Hill, 1997; R. Duda, P. Hart, D. Stork, "Pattern Classification", Wiley, 2000. N. Cristianini, J. Shawe-Taylor, "Introduction to Support Vector Machines", Cambridge University Press, 2000; T. Kohonen, "Self-Organizing Maps", Springer-Verlag, 2001; and Bishop, "Neural Networks for Pattern Recognition", Oxford University Press, 1997. Those references are specifically incorporated by reference herein.

Example 2

System Hardware

FIG. 1 depicts an example of one embodiment of a hardware device for use with the systems and methods described herein that can streamline data capture for the purpose of building a database of behavioral information.

To this end, the depicted apparatus comprises a plurality of detectors for detecting physical and biological responses. Various types of sensors may be used to collect and generate data for specific responses, and the types and arrangements of sensors employed may vary according to the application. For example, sensors may be provided for vocal recording, visual recording of the test subject's activities as well as for recording biological data of the test subject. These sensors may be external devices, or optionally, some of these devices may be implanted in or remain outside the test subject. Additionally, some sensors may be partly implanted into the specimen and partly external. In any case, the depicted apparatus provides sufficient sensor functionality to capture sufficient information that the behavioral and ideally also the physiological state of the specimen may be determined. The information collected by the sensors may be processed by a data processing device that can filter and analyze the data being collected by these sensors.

One specific system for assessing behavior of a test subject in accordance with the present invention is identified generally by the numeral 1 in FIG. 1. A video unit 2 captures video information. Optionally, a second camera may be provided to expand the angle of vision, and gain a measure of depth. A series of other devices 3 capture data pertaining to feeding, drinking, body weight, heart rate, respiration rate, operant responses and other physical characteristics and the like. This set of non-visual signals is sent to a Coordination/Time Stamp device 4 that can create a data header that can be applied to the collected data. Optionally, the information from the video unit 2 is sent to a Frame Subtraction Device 5, and to a storage primary database 6, that will compare two frames and identify the active pixels. By detecting the change in active pixels, the system may generate a measure of the motion that is occurring within the field of vision of the visual sensor. Motion detection can be achieved according to any of the known techniques, including, but not limited to, those techniques discussed in U.S. Pat. No. 5,493,344 issued to Yu on Feb. 20, 1996. In this patent, a system is described that estimates movement within a video signal to half-pixel accuracy. The described system includes a first motion detector that receives a block of video data as well as subsequent block of video data for a defined search area. Motion is detected by determining the difference between the first video block and the subsequent video blocks in the search area. A motion vector generator receives the first and the second motion vector signals and vector-sums the received signals to output the vector-summed result as a final motion vector. The vector sum operation can occur on a pixel-by-pixel basis. Although this is one technique for determining presence and motion within a search area, other techniques are also known and any suitable method known to those with knowledge of the art may be employed Active pixels only, in one embodiment of this invention, are also sent to Primary Database 6 for storage and later re-analysis. The database can be any suitable database system, including the commercially available Microsoft Access database, and can be a local or distributed database system. The design and development of suitable database systems are described in McGovern et al., A Guide To Sybase and SQL Server, Addison-Wesley (1993). The database can be supported by any suitable persistent data memory, such as a hard disk drive, RAID system, tape drive system, floppy diskette, or any other suitable system. Active pixels from the Frame Subtraction device are also sent to an Outline Fitting Device 7. The information captured by Device 7 is then sent to the Coordination/Time Stamp Device 4, where video and non-video data are synchronized. The synchronized dataset is then sent to Secondary Database 8, where data mining is performed as described below.

Figure 2:
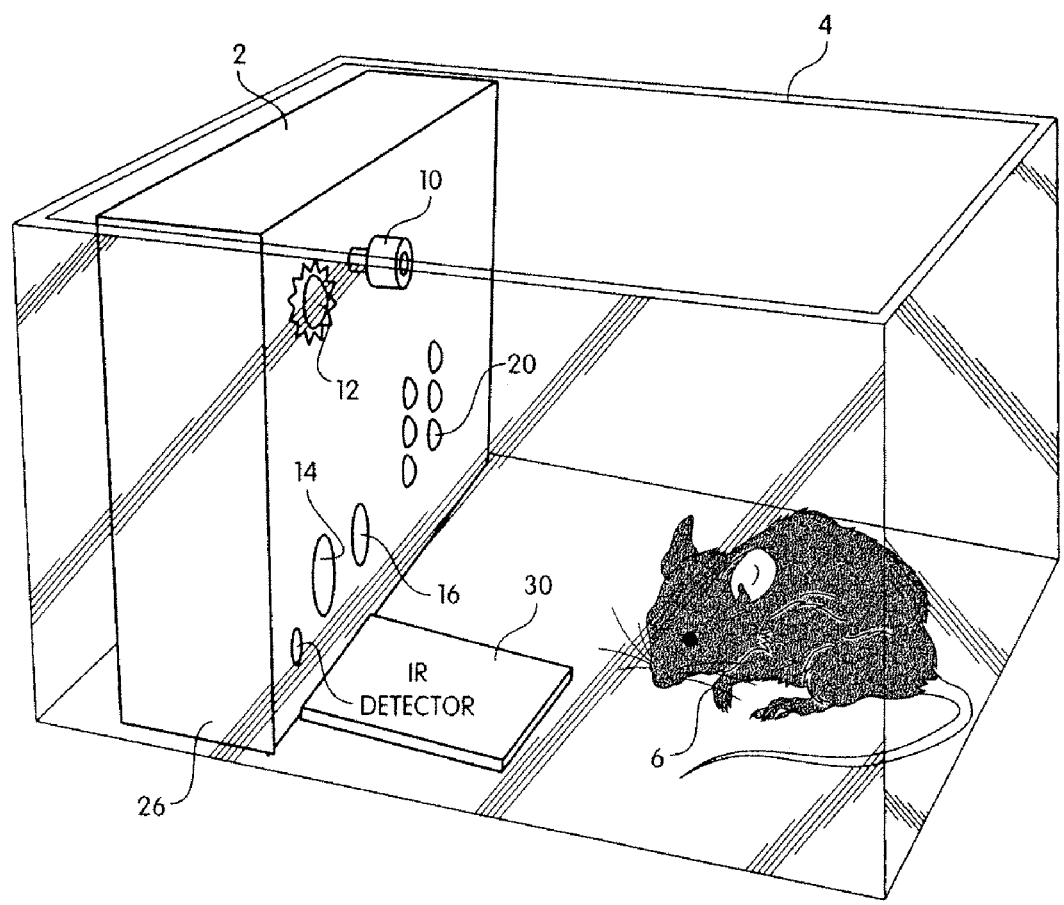
FIG. 2 is a top view of the laboratory cage illustrating the portability of the system.

In a preferred embodiment, the system 1 is defined as in FIG. 2 by a module 2 that is disposed in a cage 4. Cage 4 can be any housing, habitat, or confined area that houses the test subject 6. However, it will be understood that the systems and methods described herein can include more open environments, such as aviaries, dens, and even parklands. These embodiments may be more suited to measuring behavior related to group behavior, where more expansive monitoring environments are appropriate. Note that this module 2 design represents merely one embodiment of systems and methods of the invention and in alternative embodiments the systems described herein can include cage systems that have the sensors and other features of the module 2 integrated into the cage itself. The positioning of the depicted module 2 in cage 4 is such that the module is easily removed from the cage. The portability of this embodiment allows the module to be placed in other cages thereby allowing behavioral testing on laboratory animals in their own habitat. Module 2 is preferably sized so that it fits inside standard laboratory cages. Thus, test subject 6, depicted in this illustration as a mouse, need not be transferred from a familiar environment to an unfamiliar environment for behavioral testing to be conducted since such a move could itself influence behavior. In addition, the module can be removed for proper cleaning of the cage 4. Preferably, the module can be sterilized as well. Test subject 6 can be any test subject and need not be limited to a laboratory mouse. For example, the test subject includes, but is not limited to, humans, monkey, dogs, horses, sheep, and the like. Moreover, in embodiments where other than mammals are to be tested, such as fish, or birds, the systems of the invention can be integrated into an aquarium or into a birdcage or even an aviary. This is particularly true for those applications where the behavior information being monitored includes group behavior, mating behavior or parent-child behavior or some other complex behavior.

Module 2 further includes a base 26. Preferably, base 26 is disposed on floor 34 such that the base is level with the floor 34. However, the module 2 need not be level for operation of the module. Base 26 is such that it can house a variety of sensory devices. For example, illustrated in FIGS. 1 and 2, a video camera 10 can record the activity of the test subject 6.

A light source 12 housed in module 2 provides light to the test subject as well as a means of stimulating the test subject. Food and water is provided to the test subject in this example by access to a water bottle 14 and a food dispenser 16. Opening a door enables access. Doors are normally open, so that in case of a power failure, access will be enabled and test subjects will not be left without food and water. When access is enabled an infrared device or some other sensor will monitor the test subject's entry into the food or water opening or its access of food and water. A visual cue 20 provides the test subject with visual stimulus.

Further included in module 2 are one or more sensors 22. As depicted in this illustration sensor 22 is housed in base 26, however it need not be for the invention to function. For example, the sensor may be implanted in the test subject. The sensor may include for example an infrared (IR) or radio frequency (RF) sensor to monitor the test subjects movement and temperature. Depending on the implementation, the sensor may also include a pressure transducer such as a piezoelectric sensor for measuring the pressure applied by the test subject. In addition, a mechanical actuator 24 or operandum, depicted here as a lever, provides a mechanical device that can be used to train the subject in conditioning experiments, by, for example, requiring one or more responses to enable the feeder or the water bottle. The actuator 24, depending on the implementation, can also include a force transducer to measure the force exerted by the test subject 6, a push button, a hole monitored by an infrared beam (a "nose poke") and other like devices.

In this embodiment, a scale 30 is positioned on the base such that the test subject is weighed when seeking nutriments or interacting with any of the stimuli on the base 26. Scale 30 may further include a sensor 32. Depicted in this illustration, sensor 32 is a sensor pad for detecting electrophysiological responses of the test subject, such as an electrocardiogram. The sensor pad may also include other types of monitoring functions such as blood pressure and temperature monitoring through the use of telemetric devices and the like.

Module 2 also includes a communication link 36. Link 36 is preferably a data link. Such data link can alternatively be, but is not limited to, an electronic data link, optical fiber connection, fire wire, a network connection, a serial connection, a parallel connection, USB, wireless data connection or any other known connection used for data transfer. Depending upon the implementation, link 36 can operate in one or more modes of transmission. For example, such modes include radio frequency transmissions, optical transmission, microwave transmission, digital or analog transmission, or other known data transmission mode. The function of link 36 is to transmit and receive data to and from the module 2 by a user or computer. Depending on the implementation, the link 36 may also be coupled to several modules to provide a network of modules all connected to a central control unit or processor (not shown in FIG. 1). In addition, the processor may or may not be located inside the base 26 of module 2 as convenient. For purposes of this description, the term "processor" shall refer to any type of processor, network, server, terminal, mainframe, website, personal digital assistant (PDA), and other such electronic device, regardless if the device is wireless or wire connected. In a further alternative embodiment, the data processing system can comprise a micro-controller system. The micro controller system can also be embedded into a processing system. The micro-controller can comprise any of the commercially available microcontrollers including the 8051 and 6811 class controllers. The micro controllers can execute programs for implementing the processing functions, including the image processing functions, as well as for controlling the elements of the system, such as by executing motor control processes and feedback processes. Optionally, the data processing system can also include signal processing systems for performing the image processing. These systems can include any of the digital signal processors (DIPS) capable of implementing the image processing functions described herein, such as the DIPS based on the TMS320 core including those sold and manufactured by the Texas Instruments Company of Austin, Tex.

FIG. 2 illustrates in accordance with this example of the present invention the layout of the module 2 with respect to cage 4. The test subject 6 is allowed to freely roam in an open playing field on floor 34. The test subject may be manipulated while in this open playing field. Such manipulation can include surgical procedures, genetic alterations, physical challenges and the like. A resting or nest area 40 is also provided in cage 4 so that the test subject 6 is maintained in the habitat it has become accustomed to while being tested for behavioral characteristics. The module 2 is disposed in the opposite portion of the cage 4 from the nest area 40 to allow the test subject 6 free roam in the playing field. This positioning assists in reducing the stress to the test subject and decreases the incidence of obtaining erroneous data from removing the test subject to another area or cage for behavioral testing.

Figure 3:
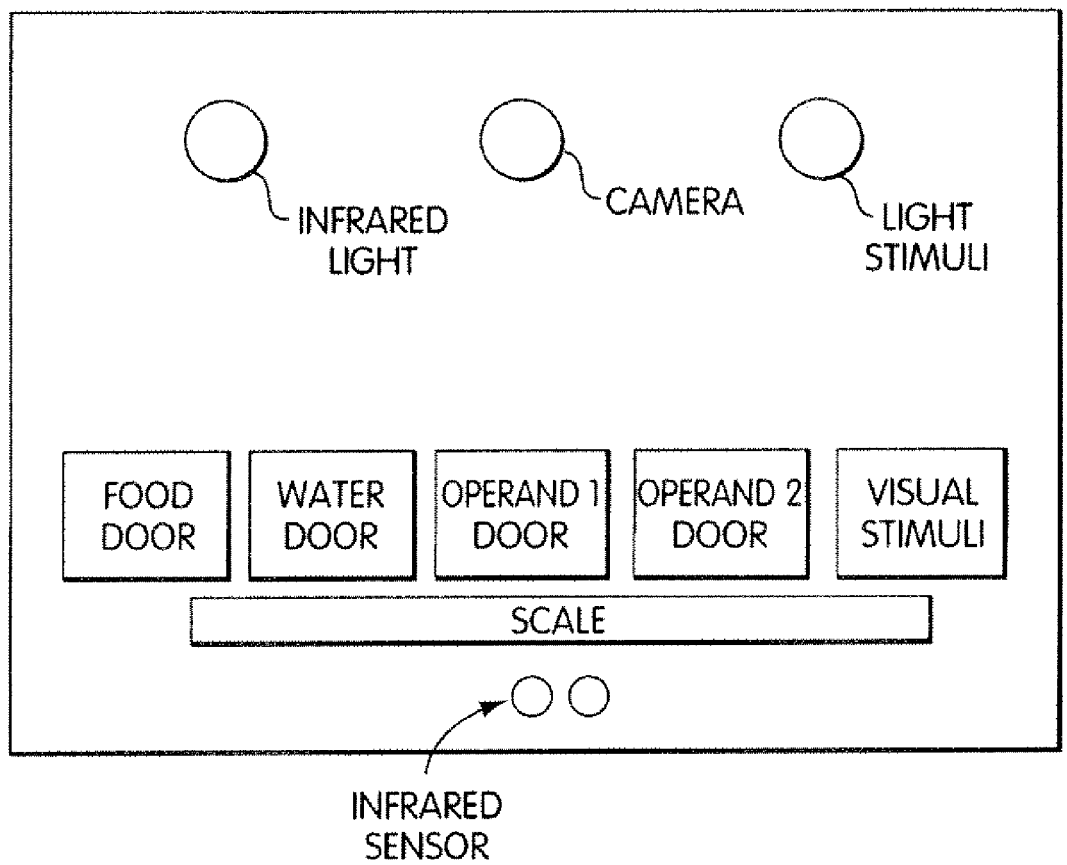
FIG. 3 is a front view of the laboratory cage illustrating the main experimental module.

FIG. 3 is a front view of the module 2. In this alternative example a possible disposition of the stimuli and other features is shown. A low-lux wide-angle video camera 10 can record the test subject's activity throughout the day and night. The cameras may record the test subject's activity of eating from food dispenser 16 and drinking from water bottle 14. A scale 30 can measure body weight or simply sense the presence of the mouse on that side of the cage. One or two operanda are used to condition the animal or measure motor strength. If access to the operanda must be restricted, doors 37 and 38 similar to the food 16 and water doors 14 can be implemented. Visual stimuli can be presented on a screen 35. Additional visual stimulation is provided by a Light source 12. Infrared light for night recording is provided by infrared lamp 36. Additionally, sensors as previously described may also be used to monitor the physical and biological effects of the projection screen on the test subject.

In another embodiment, the subject system utilizes 3 or more cameras; a top camera and two or more side-view cameras. A top camera is used to locate the animal in the cage or other enclosure, e.g., it provides the X-Y coordinates of the animal. Information from that camera can also be used to determine certain body shapes, e.g., stretching, curled, etc., as well as position relative to cage structures (food, water bottle, air puffing valves, etc). That camera can also provide information concerning rate and direction of travel, including rotations. In certain optional embodiments, the top camera is also used to determine which side-view camera(s) to use to see the profile of the animal. Collectively, the top and profile information can be used to determine most if not all of the fine and gross bodily movements of the animal. In certain preferred embodiments, standard NTSC or PAL video is used. In certain preferred embodiments, video capture occurs at a rate of at least 30 frames/second, in order to see fast activity of the animal such as startle response or twitching. In some embodiments, the subject systems employ LED or other flicker-free lighting (such as high frequency fluorescent lights), and preferably uses lighting that has instant on-off response and low heating ratings.

In certain embodiments, the subject system and method can include one or more sensory devices for use with the various behavioral experiments described above, as well as other such behavioral experiments. The sensory devices transmit the data to a processing device that collects the behavioral and physiological data to give a behavioral assessment of the test subject.

Typically, a sensor involves the use of a transducer that detects and measures changes in the environment. The sensor produces a variable signal, usually a voltage that changes in a linear manner the feature that is being measured varies. Some sensors produce an output, called the back signal or back voltage, that can be used in a feedback loop to reduce or increase whatever variable is being applied to create the change. The loop configuration acts as a limiter that minimizes the possibility of damage to objects tested. For example, in the context of laboratory animals being exposed to an experimental drug intravenously (IV), the sensor could detect harmful effects of an experimental drug to the test subject. Reduction of the IV dosage of the experimental drug could be initiated by this loop function. This function is referred to as a limiter that can reduce the chance of injury to the test subject. Another example to this feedback loop feature is in rewarding the test subject. For example, upon a detected appropriate response of the test subject, activation of a food source can supply the test subject with a reward.

In certain embodiments, the system includes a sub-system for detecting ambulatory and non-ambulatory movements. To illustrate, the cage can be equipped with an array of infrared sensors producing a beam pattern in the cage of high enough resolution to differentiate between ambulatory and non-ambulatory movements for both rats and mice. Status about IR beam interruptions by the animals is transferred from all sensors to the computer system. From the received information about beams interruption, the system computes the number of ambulatory and non-ambulatory animal movements as well as animal position along each sensor.

The system may also include a foot misplacement apparatus. This apparatus can be used to measure sensory-motor function. An exemplary embodiment of such a system may consist of a set of two stainless steel horizontal ladders. The spacing of the rungs on each ladder is different to accommodate both rats and mice. At one end of the ladder, a dark compartment exists to entice the animal to walk toward the perceived "safety" of the dark cover. The apparatus provides an electric conditioning stimulus for training the animal by punishing them if they touch the metal plate, which is located below the horizontal ladder. After the animal is conditioned, an actual test is performed by placing the animal on one end of the ladder, and counting the number of missteps as it moves toward the dark compartment at the other end of the ladder. Counting missteps is done automatically by detecting the change of resistance between the ladder and the metal plate. Each time the animal misses one of the rungs of the ladder and touches the metal plate below; a very small electric current is detected, amplified, and counted by a separate computerized counter. The animal is not aware of this current, as it is far below the threshold of the animal's sensitivity.

The present system may be used with a variety of tests for cognitive function, especially learning and memory testing, and are preferably carried using an automated system. Learning and/or memory tests that can be used to generate data for the subject databases include, for example, inhibitory avoidance, contextual fear conditioning, visual delay non-match to sample, spatial delay non-match to sample, visual discrimination, Barnes circular maze, Morris water maze, and radial arm maze tests.

An exemplary passive avoidance test utilizes an apparatus that consists of a lit chamber that can be separated from a dark chamber by a sliding door. At training, the animal is placed in the lit chamber for some period of time, and the door is opened. The animal moves to the dark chamber after a short delay—the latency—that is recorded. Upon entry into the dark chamber, the door is shut closed and a foot shock is delivered. Retention of the experience is determined after various time intervals, e.g., 24 or 48 hours, by repeating the test and recording the latency. The protocol is one of many variants of the passive avoidance procedures (for further review, see Rush (1988) Behav Neural Biol 50:255).

An exemplary maze-testing embodiment is the water maze working memory test. In general, the method utilizes an apparatus that consists of a circular water tank. The water in the tank is made cloudy by the addition of milk powder. A clear plexiglass platform, supported by a movable stand rest on the bottom of the tank, is submerged just below the water surface. Normally, a swimming rat cannot perceive the location of the platform but it may recall it from a previous experience and training, unless it suffers from some memory impairment. The time taken to locate the platform is measured and referred to as the latency. During the experiment, all orientational cues such as ceiling lights, etc., remain unchanged. Longer latencies are generally observed with rats with some impairment to their memory.

Another memory test includes the eyeblink conditioning test, which involves the administration of white noise or steady tone that precedes a mild air puff that stimulates the subject's eyeblink.

Still another memory test that can be used is fear conditioning, e.g., either "cued" and "contextual" fear conditioning. In one embodiment, a freeze monitor administers a sequence of stimuli (sounds, shock) and then records a series of latencies measuring the recovery from shock induced freezing of the animal.

Another memory test for the test animals is a holeboard test, which utilizes a rotating holeboard apparatus containing (four) open holes arranged in a 4-corner configuration in the floor of the test enclosure. A mouse is trained to poke its head into a hole and retrieve a food reward from a "baited" hole that contains a reward on every trial. There is a food reward (e.g., a Fruit Loop) in every exposed hole that is made inaccessible by being placed under a screen. The screen allows the odor of the reward to emanate from the hole, but does not allow access to the reinforcer. When an individual hole is baited, a reward is placed on top of the screen, where it is accessible. The entire apparatus rests on a turntable so that it may be rotated easily to eliminate reliance on proximal (e.g., olfactory) cues. A start tube is placed in the center of the apparatus. The subject is released from the tube and allowed to explore for the baited ("correct") hole.

The subject system can include precision food consumption monitors, preferably a monitor with accuracy of 10 mg. In an illustrative embodiment, the design of the animal feeders assure very high accuracy of measurements by prohibiting the animals from removing food pellets from the feeding dish or bringing in debris. For instance, the feeder can be placed outside the animal cage; the animal can access it only via a narrow channel, face first. Measurement of food consumption is accomplished by weighing the food dish with precision electronic scales, and interfaced to a computer system for automation.

The system can also include $VO_2/VCO_2$ monitors. For instance, the system can include an indirect open circuit calorimeter designed to simultaneously measure metabolic performance of multiple subjects that have differing ventilation needs. The system monitors oxygen and carbon dioxide concentrations by volume at the inlet and outlet ports of a chamber/canopy/tent/mask through which a known flow of air is being forcibly ventilated. The difference in gas concentrations along with flow information is employed in the calculations of oxygen consumption, carbon dioxide production, respiratory exchange ratio and heat.

In certain embodiments, the subject system will include a volumetric drinking monitor, e.g., that can precisely measures the volume of liquid consumed by laboratory animals (rats, mice, etc.) with resolution of one drop. In an exemplary embodiment, the monitor is controlled by a computer system that logs results in periodic intervals. The subject drinking monitor can be combined with a precision solid (or paste) food consumption monitor and/or with $VO_2/VCO_2$ monitors for comprehensive animal metabolic evaluation.

The system can also include an "anxiometer", e.g., a system designed to induce anxiety within a subject and monitor the degree of drug effect. In an illustrative embodiment, the anxiety is induced in the animal by the administration of a mild shock after a certain number of licks on a sipper tube. The shock is delivered through the sipper tube and is maintained for two seconds. With the onset of the initial shock, the system begins a three-minute testing session during which the total number of licks and shocks (administered with every nth lick) is recorded by the system. The performance of anti-anxiety drugs, for example, can be measured by comparing the drinking behavior of punished drugged rats to the behavior of punished non-drugged rats.

In certain embodiments, the subject system also includes a sub-system for quantify convulsive activity in small laboratory animals. In an exemplary embodiment, an unrestrained animal is placed within a chamber that resides upon a sensing platform. The platform is connected to a load sensor that converts the vertical component of motion into an electrical signal. The instrument accumulates impulse counts and time. An impulse count is accrued for each gram-second (980 dynes) of force applied to the sensing platform, and terminates monitoring at the conclusion of the episode. In preferred embodiments, the instrument responds only to changes in the force exerted on the platform. The static force exerted by the weight of the platform and animal is not recorded.

The subject system can also include a cold/hot plate analgesia measuring system, e.g., which utilizes a metal plate that can be heated and cooled. An animal's sensitivity to pain resulting from exposure to heat or cold is tested by placing the animal on the surface of the plate and starting a built-in timer. The timer is stopped at the instant the animal lifts a paw from the plate, reacting to the discomfort. Animal reaction time is a measurement of animal resistance to pain and is used to measure efficacy of analgesics, or side-effects involving impairment of the central or peripheral nervous system.

In certain embodiments, the subject system includes a grip strength meter, e.g., for assessing neuromuscular function by sensing the peak amount of force an animal applies in grasping specially designed pull bar assemblies. Metering can be performed with precision force gauges. The values may be either recorded manually or automatically via a computer interface. Fore and hind limb assessments can be performed concurrently with the dual sensor models or they can be performed in separate trials with the single stand model. In practice, the dual sensor model is employed by first allowing the animal to grasp the forelimb pull bar assembly. The animal is then drawn along a straight line leading away from the sensor. The animal will release at some point and the maximum force attained will be stored on the display. The animal continues to be moved along until the rear limbs grasp the second pull bar assembly. Again, there will be some point at which the animal releases after which the second sensor will retain the hind limb grip strength.

The system can also measure startle reflex. For instance, it may include an instrument for quantifying the vertical component of motion associated with the startle reflex. The assessment of the startle reflex can be an indicator in evaluating sensory and CNS performance. In practice, the subject is presented with some type of stimuli: acoustic, tactile or electric shock while situated on a device that records motion. The recorded parameters are: latency from stimulus onset to response and magnitude of response. The subject system can employ a single point load cell for the measurement of motion. This device is attached to a platform on which the animal is housed in such a fashion as to allow free movement. The single point design of the sensor assures equivalent measurements regardless of animal location. The sensors are manufactured to precise standards that yield linear performance, wide dynamic range and matched performance that eliminates the need for repeated calibration.

Whether acquired in an automated fashion or not, it is specifically contemplated that such data can be included in the data models of the present invention. There are a variety of other behavioral response for which automated and semi-automated data acquisition can be accomplished by the apparatus of the present invention, and include:

Tail Suspension: Indicator of dysfunction in descending motor pathways.

Orientation, direction of turning, and fore and hindlimb spasticity are evaluated.

Grid Walk Test: Stride length, walking foot spread and resting foot spread are measured in this test of limb coordination. Especially sensitive to deficits in descending motor control.

Beam Walking: Assessment of motor incoordination. Time required for an animal to pull itself into a balanced position on a narrow beam is recorded.

Rotarod: Tests an animal's ability to remain on a rotating rod as the speed of rotation increases. Requires a high degree of sensorimotor coordination and is sensitive to damage in the basal ganglia and the cerebellum. Differentiates analgesia from sedation.

Grip Strength: Forelimb and hindlimb muscle strength evaluated by the distance a bar on a strain gauge is pulled before paw-grip is released.

Landing Foot Spread: Test of peripheral nerve damage (neuropathy). The animal is released from a height, and the distance between the hindfeet as the animal lands is recorded.

Skilled Reaching (forelimb motor control): Rats reach through a small opening to retrieve food pellets. Sensitive to moderate to severe DA depletion caused by unilateral 6-OHDA.

Forelimb Asymmetry: Weight shifting using forelimbs during vertical exploration and landing in a cylinder. Sensitive to non-severe levels of DA depletion and to L-DOPA.

Bilateral Tactile Stimulation (2 phase): Assays forelimb tactile sensation, in which an adhesive patch is applied to the wrist of each forelimb, and the order and latency of stimulus removal is recorded. Sensitive to severe levels of DA depletion.

Single Limb Akinesia: Movement initiation in which direction of steps and stepping movements are assessed. Sensitive to direct DA agonists when degeneration of DA neurons is not severe.

Placing Test: Asymmetries in forelimb placing, following unilateral 6-OHDA, using vibrissae-elicited placing.

Bracing Test: Evaluates capacity to adjust stepping and regain postural stability when rapid weight shifts are imposed. Sensitive to DA agonists, even when degeneration is severe.

Orienting Movement: Measures latency to orient to a tactile stimulus (right or left side of face). Sensitive to moderate to severe DA depletion.

Disengage Test: Orienting test (above) conducted while animal is eating. Sensitive to a moderate level of DA depletion.

Drug-Induced Turning (rotational test): Number and direction of horizontal circling movements following apomorphine. Common test for screening potential therapies when DA loss is severe.

Activity changes following MPTP (mice): Automated recording of both locomotor and rearing activity.

von Frey Threshold: Sensitivity to graded mechanical stimulation by monofilaments.

Allodynia/place avoidance: Mechanical hyperalgesia (monofilament stimulation) in response to nerve injury, combined with avoidance of environment in which the pain occurred. Measures both sensory and affective components of neuropathic pain.

Elevated Plus-Maze: Standard test of anxiety in which the animal is placed in the center of an elevated 4-arm maze where only two of the arms are enclosed. Anxiety-related behaviour is measured as avoidance of the open arms.

Maternal Separation: Anxiety test in which ultrasonic distress vocalizations are counted in juvenile pups that have been separated from their mother.

Light/Dark Preference (Emergence Neophobia): Activity in light and dark portions of a box are recorded. Avoidance of lighted portion reflects elevated anxiety while little or no time in the dark area reflects limbic disruption and certain brain lesions.

Intravenous Self-Administration: Animals learn to lever press for an infusion of a compound, via an intravenous catheter. Measures reinforcing effects of drugs of abuse or potential addictive properties of new pharmacological compounds.

Intracranial Self-Stimulation: Animals lever press to stimulate brain regions involved in reward. Measures drug effects on reward.

Straight Alley: Animals run from a "start" box to a "goal" box, by way of a straight alley, to receive a drug infusion. Latency to reach the goal box reflects the motivation of the animal for the drug.

Place Conditioning: Evaluates preference or aversion of an animal for an environment that has been associated with a positive or negative stimulus, usually a drug or a mild shock. It is performed in a box with two distinguishable environments separated by an alley. This test has been used to study learning and memory, as well as the reinforcing effects and potential addictive properties of drugs of abuse.

Locomotor Activity: Measured in activity boxes, in which photobeams measure locomotion. Changes in locomotor activity over repeated injections may reflect tolerance and/or sensitization to drug effects.

Circadian Activity: Measurement of general activity in a day-night cycle. Sensitive to hypothalamic dysfunction as well as neuromuscular damage. Can also be used to measure food consumption over the circadian cycle to assess eating behaviour or non-specific drug effects.

Sleep Patterns: The different components of awake and sleep are measured using an EEG in freely moving animals. Some drugs of abuse will disrupt these patterns.

Salivary Secretion: Evaluation of autonomic function in which the degree of saliva secretion is measured.

Nest Building: Nest building capability and complexity. Reflects frontal cortex or limbic system damage.

Food Hoarding: Relationship of food pellet size to the tendency to carry it back to the animal's home area. Sensitive to frontal cortex damage.

Food Wrenching and Dodging Test: Aggressive behaviour in defense of food.

Context Discrimination: A general test of associative learning, in which the animal is placed in a box with a center divider containing a gap. Food is placed in one side of the box and the animal is allowed to find and consume it, then is tested the following day for latency to enter the side that contained the food.

Pre-pulse Inhibition: A test of rats and mice ability to "gate" or inhibit the effect of environmental information. Normal animals exhibit less of a startle response to a sudden loud sound if it has been preceded by a softer sound. This phenomenon is mediated by dopamine, and its impairment may underlie attention deficits and schizophrenia.

With further reference to the figures, the module 2 is in communication with a primary database 6. Primary database 6 is used off-line to store video information and other time stamped outputs that can be reanalyzed at a later time.

The primary database 2 is in communication with a module 5 to extract important feature from the video data, as described below.

Processed video data is sent to Coordination device 4 that coordinates the visual and non-visual signals according to their time stamps. The combined information set is then sent to the secondary database 8 for further processing. This secondary database 8 can advantageously link to other databases to obtain additional information that may be required for the interpretation of behavioral, physiological and other data-mining needs. Such links may include for example, but are not limited to National Institutes of Health (NIH), Academy of Behavioral Medicine Research, Association for Behavior Analysis Society of Behavioral Medicine and text references such as Diagnostic and Statistical Manual of Mental Disorders, Fourth Edition (DSM IV).

The database may store other type of data such as gene and protein expression patterns obtained from techniques such as cDNA chips, in situs and the like. The function of the secondary database 8 is to interpret the behavioral signature of the drug or manipulation. In addition, various methods of data mining may be used to analyze the data for relationships that have not previously been discovered. For example, a "signature method" is used. FIGS. 4 to 9 illustrate the generation of a "signature".

Figure 4:
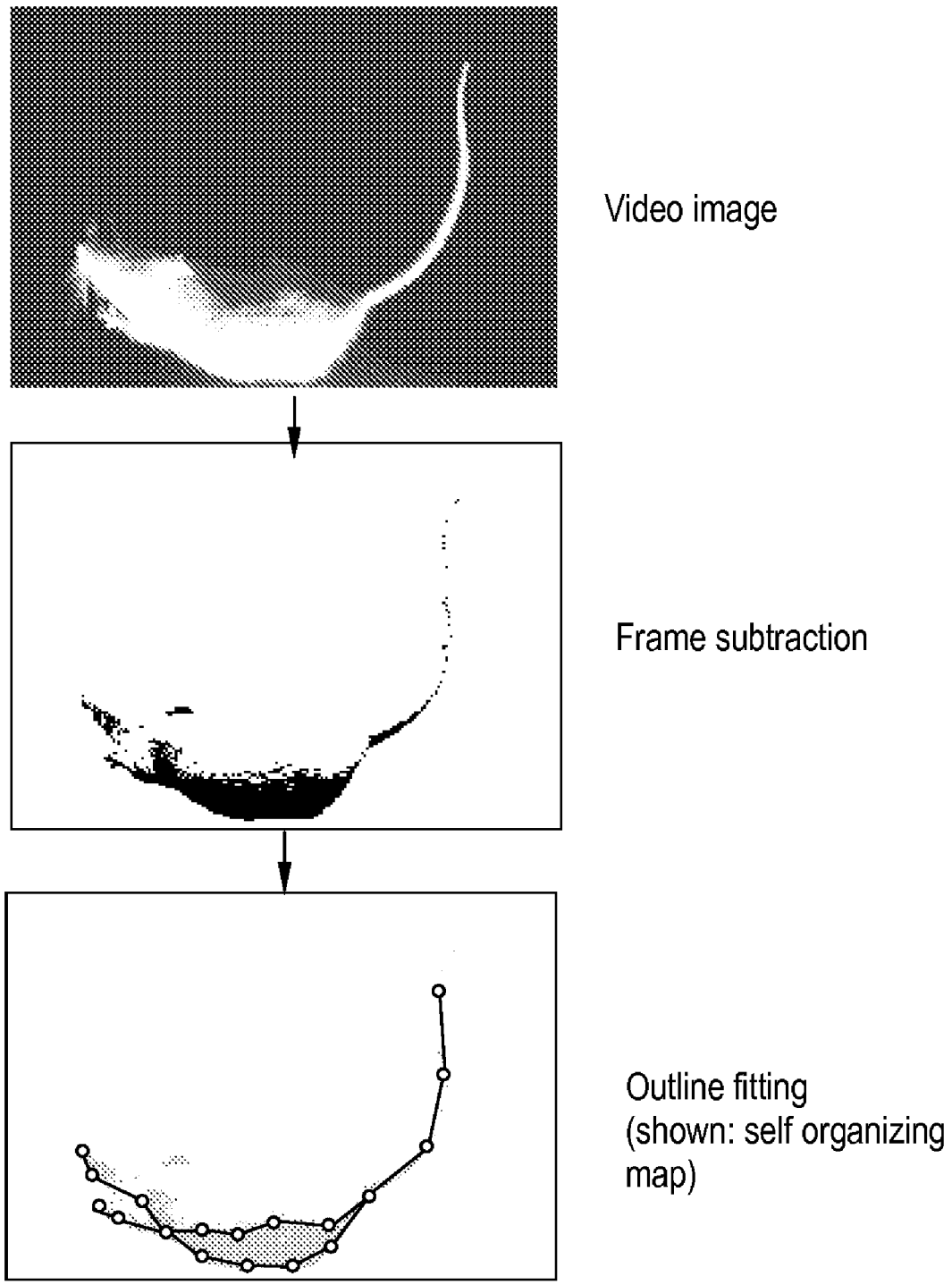
FIG. 4 is an example showing the processing of a video frame.
Figure 5:
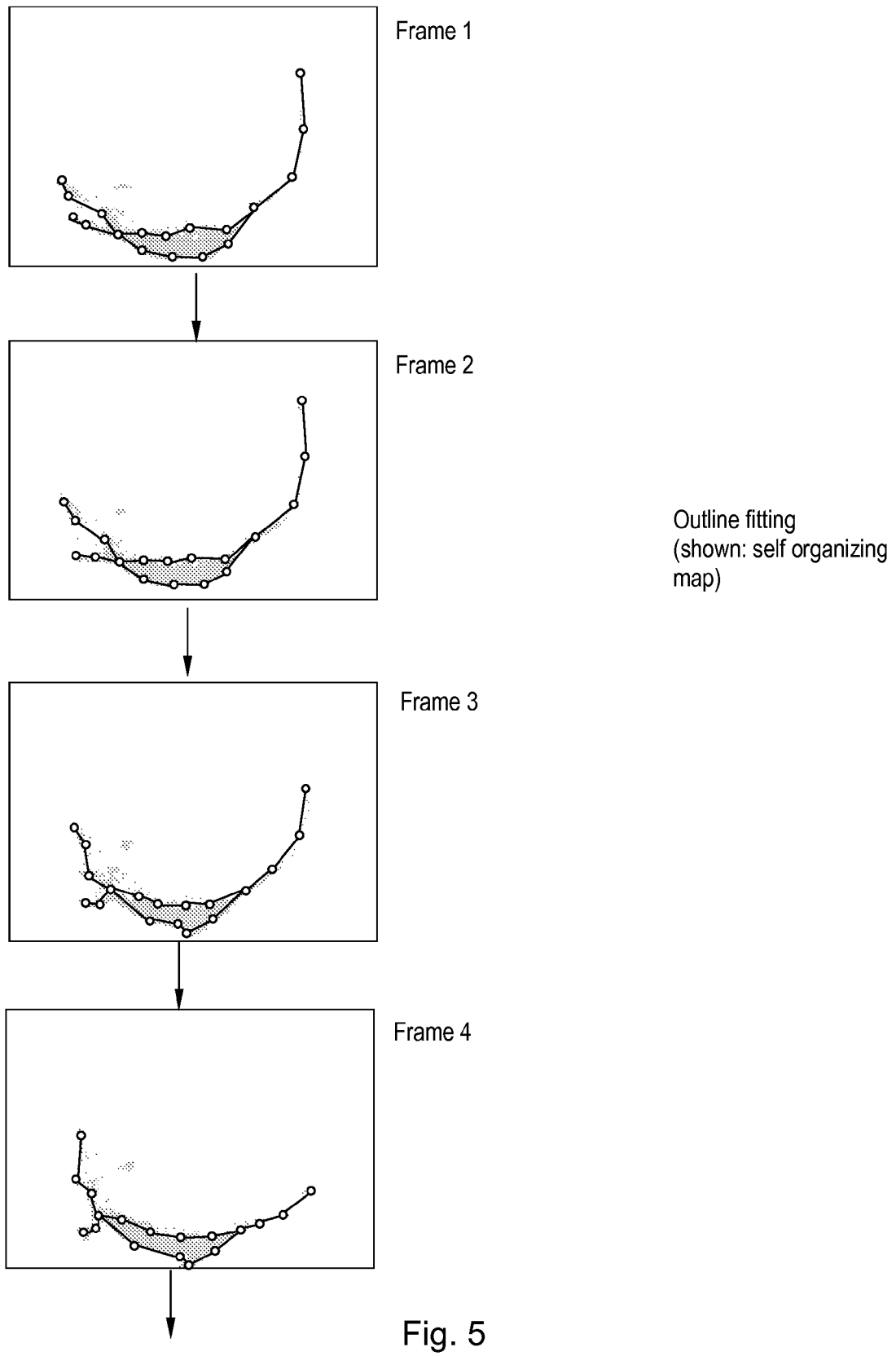
FIG. 5 is an example of the outline fitting of 4 consecutive frames.
Figure 6:
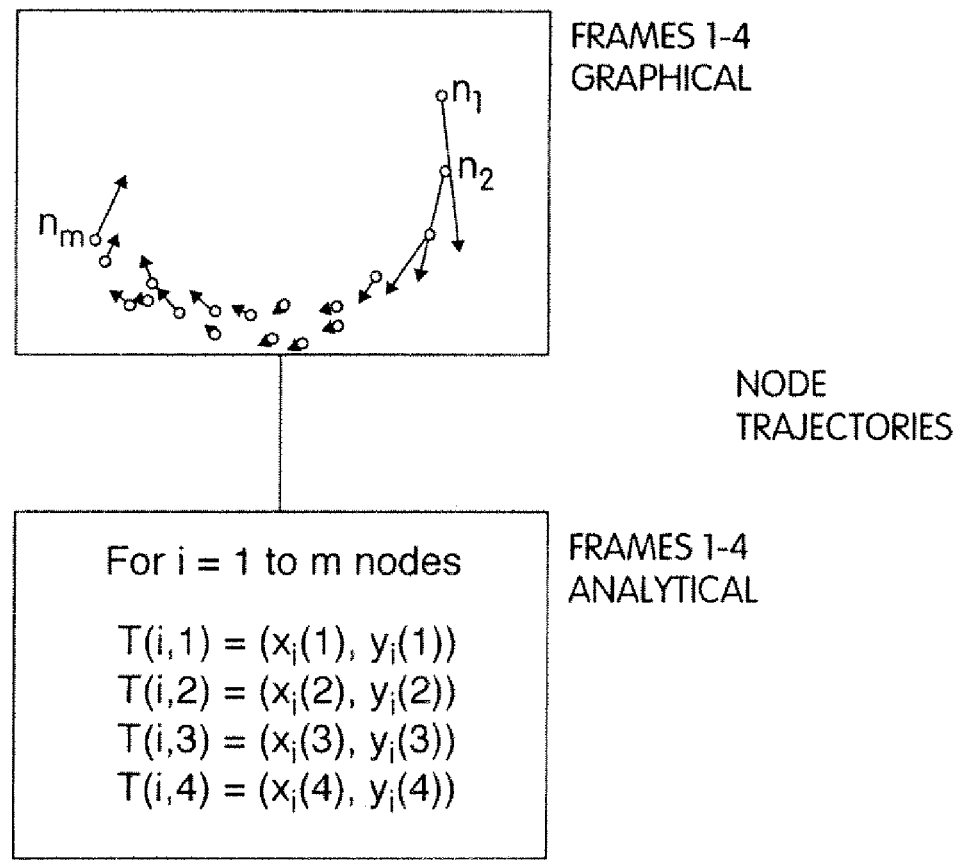
FIG. 6 is a graphic and analytical representation of the node trajectories from FIG. 5.
Figure 7:
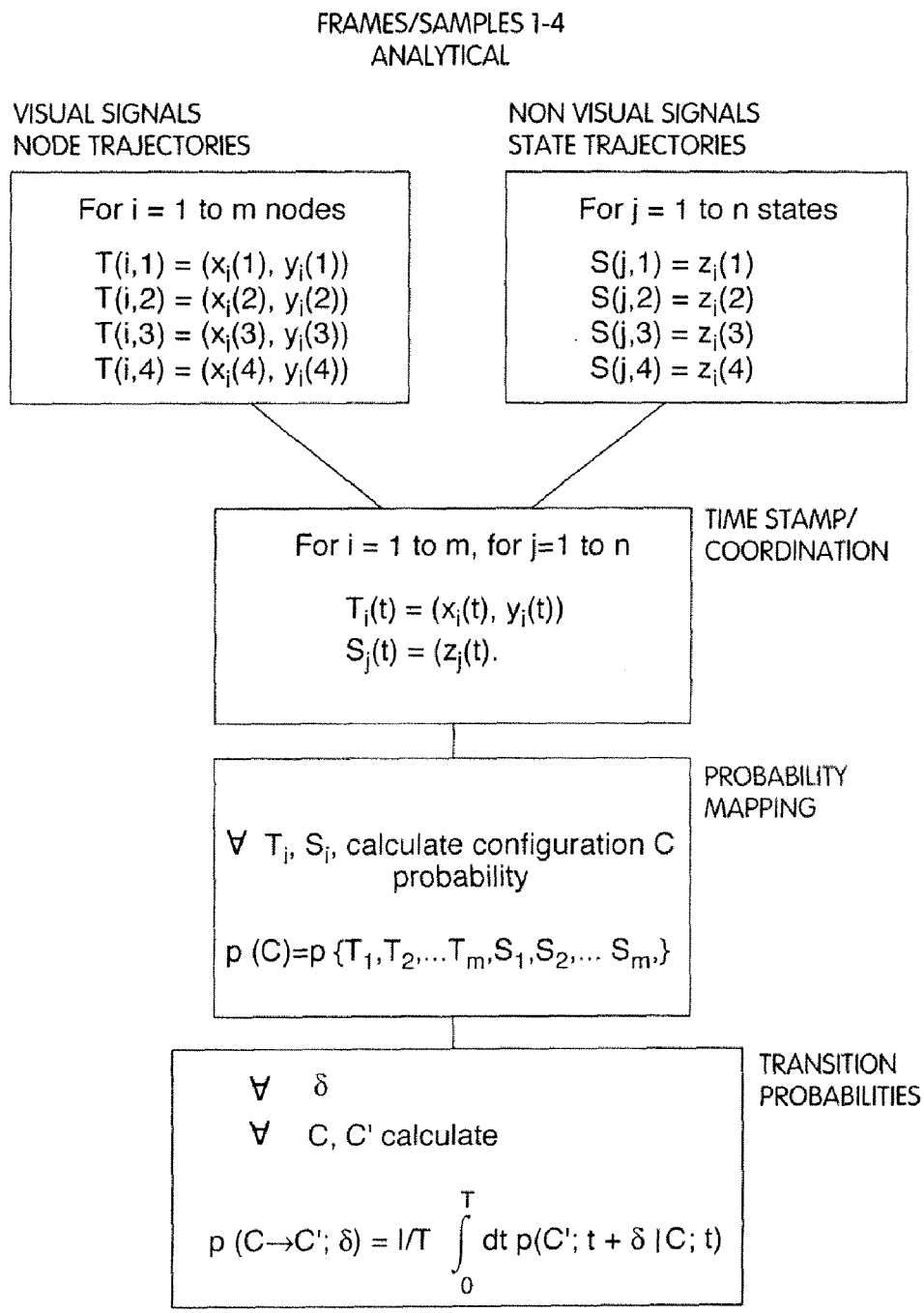
FIG. 7 is a diagram showing how the video and non-video signals are combined and time stamped.
Figure 8:
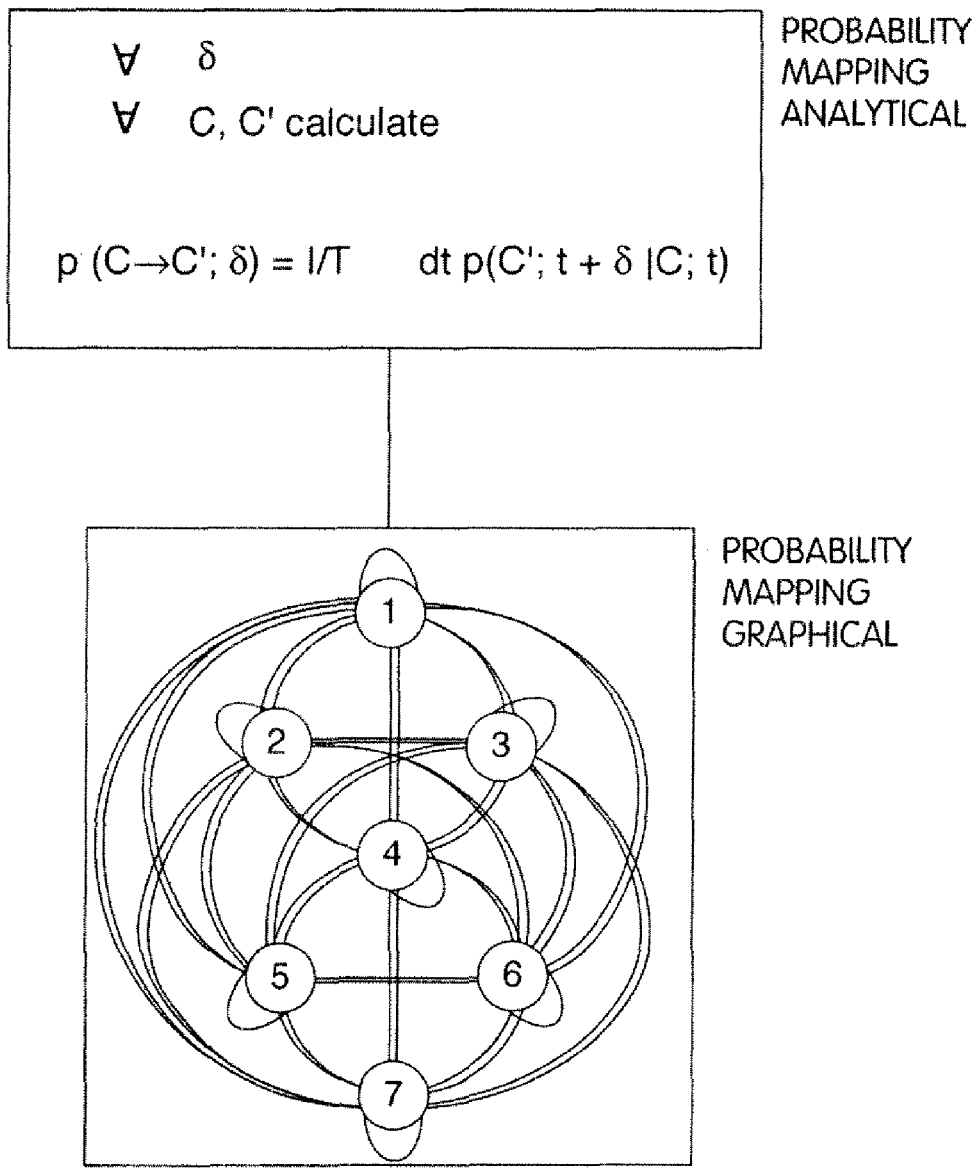
FIG. 8 is a diagram showing necessary processes to summarize the complex dataset resulting from signal combination and time stamp and the resulting state probabilities and state transition probabilities.

FIG. 4 shows an example of a video frame with the image of a mouse. The image is simplified into an outline and the outline is fitted with a self-organizing map (SOM) that tracks the outline. SOM minimizes the distance between the active pixels and a number of nodes. The position of the nodes can then be monitored over different frames. Other fitting methods can be used including ellipse and spline fitting and the like. In the example, the SOM is shown in FIG. 5 tracking the outline of a mouse over 4 different frames. Some of the nodes will track the movement of the back of the animal, while other will track the large movements and more subtle changes in the position of the tail, nose, extremities, chest, ears, etc. Large and small movements will be captured. Large movements will include locomotion, rearing, circling and the like. Small movements may include but are not restricted to sniffing, ear twitching, respiration, tail shakes and others. FIG. 6. shows the node trajectories obtained from the positioning of the nodes in the SOM. The node trajectories are combined with non-visual data coming out of the hardware device. In FIG. 6 the node trajectories and non-visual states (such as accessing the food or water, or a measure of body weight or the like) are combined. A certain combination of these variables is called a state if it occurs with at least certain probability. A HMM or like technique is used to assess the transition probability between, for example, 100 states. The HMM identifies combination of variables that occur with some frequency, assigns them to a state and calculates the probability of occurrence and the transition probabilities between states. An imaginary state could be a low heart rate signal, and low respiration signal and static node trajectories. Such a state may correspond to a sleeping animal, but the system does not need to recognize or name the state. As explained below, recognizing or identifying the states into standard behavioral categories is possible but not necessary to enable the invention. The transition probabilities are calculated for each dataset obtained from each animal. For every treatment, whether gene manipulation, drug treatment, strain or the like, a group of animals is typically run (for example, 10 animals may be injected with water and 10 animals with an experimental drug). State and transition probabilities as obtained from the HMM will be combined for the animals of each treatment to generate a "group" probability map. This map will then summarize the behavior of all animals in each group. As the important effects of the drug or other treatment are relative to the control group, the treatment and control groups must be combined. For example, if the treatment group shows a high probability of a state combining high heart rate, low respiration rate and no movement, and the treated experimental group show a very low probability of such state, the change in probability for that state should be calculated. This is important because in another strain of animals such probability in control animals may be very low, so the absolute value of the state probabilities is not important, but the relative change of the state probabilities between experimental treatment and control. FIG. 8 shows an example of such combination of probability maps between control and experimental animals. For simplicity the control group map is shown with 7 different equally probable states, and all transition probabilities are the same as well. The treatment probability map shows that seven transition probabilities have been affected by the treatment, three have increased and four have decreased, resulting in a high probability of state 6. Once the differential maps, or "treatment signatures" have been calculated they are stored in the secondary database. There they can be compared with other treatment signatures. Treatments with similar neurobiological mechanisms will result in similar signatures.

Using clustering techniques or the like, treatment signatures can be combined into clusters or classes. For example all anxiolytic drugs will result in similar signatures and will then be clustered together. Once the database is populated with many treatments comprising pharmacological treatment, gene manipulation treatments, lesions and the like, a cluster analysis will provide a general classification of treatments into major and minor classes. For example, antipsychotic drug treatments should result in one antipsychotic family with two different subclasses, one for typical and one for a typical antipsychotic.

Once the database is populated it can be used as a diagnostic tool by comparing the signature of a novel treatment with the existing signature classes arising from the cluster analysis. Such a comparison should result in an estimate of the similarity between the treatments. By using the appropriate statistical tools a probability that a treatment belongs to a particular cluster can be obtained. Considering the number of animals or samples taken to construct the average map for the control and treated groups, the number of existing drug classes and class member in the database, an estimate of the reliability of the diagnostic classification can also be given. This is depicted in FIG. 9 where a novel signature is compared against two other treatment signatures (although in the real process the novel signature should be compared against all signatures stored in the database). In the example a novel drug signature is compared against two existing drug class signatures that show some degree of similarity. Drug A class shows minimal similarity and the probability that the novel drug belongs to drug A class is modest (0.42) but the reliability of the estimate is very low (0.22). Drug B class shows extended similarity and therefore the probability that the novel drug belongs to drug B class is high (0.94). As the reliability of that estimate is acceptable (0.56), the classification of the novel drug into drug B class is warranted. A table such as that depicted in FIG. 9 is the end product of the invention. If the drug classes of the example were toxic drugs in drug A class and antidepressant drugs in drug B class, such a table would suggest that the novel drug is an antidepressant but it will probably have toxic side effects. Such a result may result in the termination of effort to push this drug into clinical trials, cutting cost of drug development short. As stated the invention can handle investigation of the effects of novel drugs, characterization of novel mutants created by genetic manipulation, and any other treatment. The data can be behavioral, physiological, gene expression data and the like. Monitoring of live animals may be the primary input, or data collected from tissue.

Example 3

System Hardware

Another aspect of the invention provides animal habitats (such as cages), as well as kits and modules for outfitting habitats, for automated capture of behavioral, neurological and/or physiological measurements. In certain embodiments, the subject systems are designed to be flexible and accommodate a wide variety of experimental apparatus. In certain embodiments of the habitat, the wall panels, floor and top can be replaceable modules that can be fitted with various instruments depending on the needs of the research in progress. See FIGS. 15 and 16, as one example. Additionally, the subject habitats can be designed to facilitate the conduct of as many experiments as possible during a single session without the need to exchange instrument modules. In certain preferred embodiments, the measurement devices and sensors are provided with computer or other digital or analog-to-digital interfaces.

Figure 15:
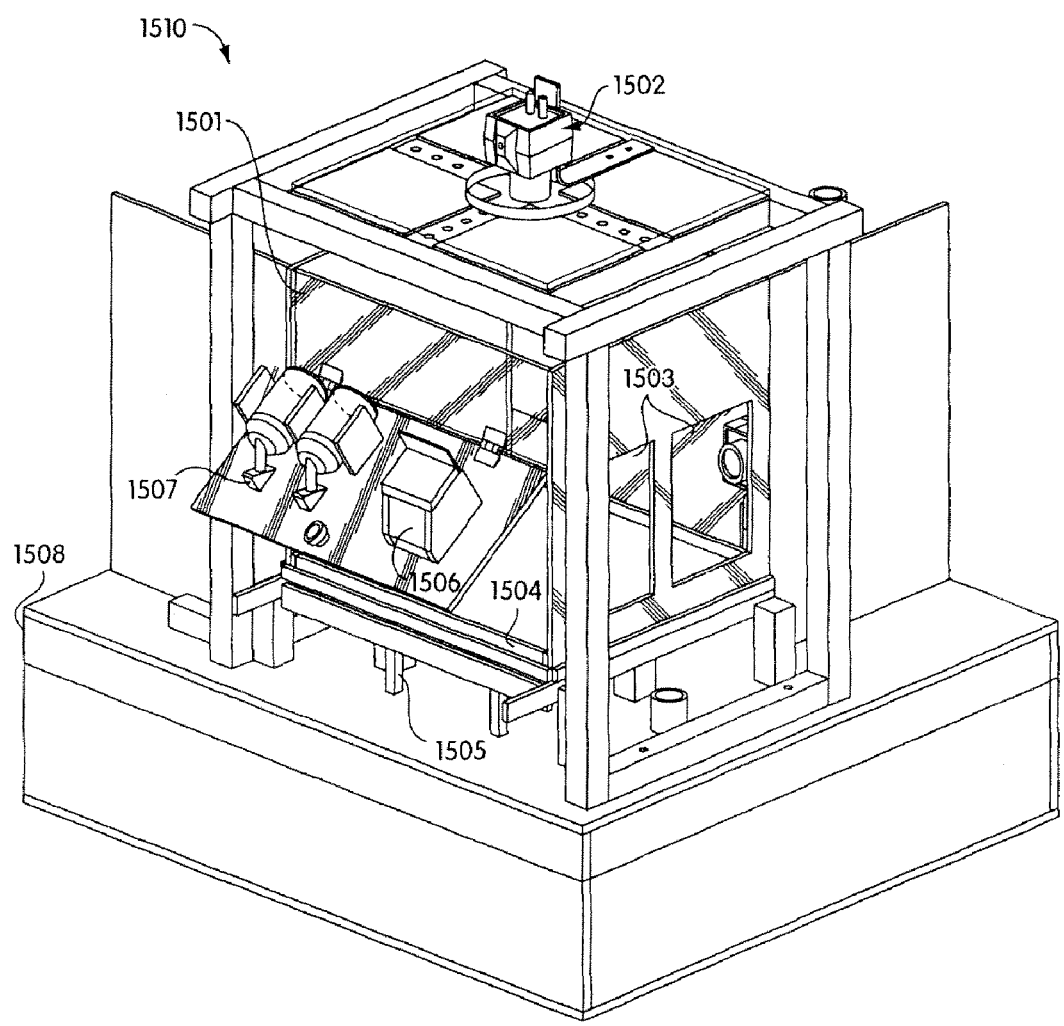
FIG. 15 shows a front perspective view of a preferred embodiment of the system.
Figure 16:
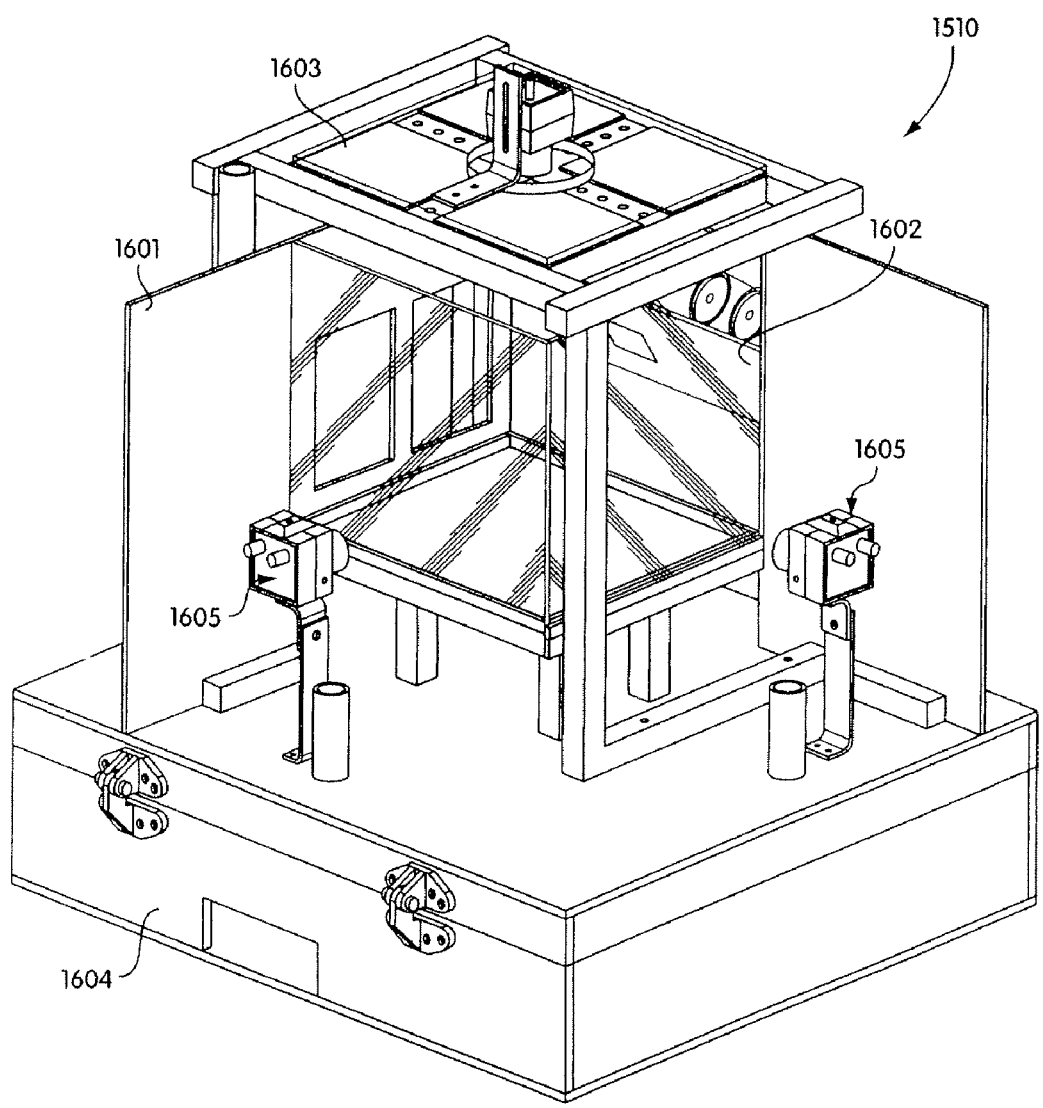
FIG. 16 shows a rear perspective view of a preferred embodiment of the system.

FIGS. 15 and 16 show different views of an exemplary animal habitat of the present invention. In the illustrated embodiment, the system 1510 includes a slide out cage 1602 having at least two clear sides. The system 1510 also includes three image capture devices (shown as cameras); a top camera 1502 and two side-view cameras 1605. The top camera 1502 provides a top view that is used to locate the animal on the floor 1504 of the cage, e.g., it provides X-Y coordinates of the animal. Information from the top camera 1502 can also be used to determine certain body shapes, e.g., to determine if the animal is stretching, curled up, etc., as well as its position relative to cage structures (food, water bottle, air puffing valves, etc). The top camera 1502 can also provide information concerning the rate and direction of travel the animal, which may be useful in identifying such behaviors as the animal walking or spinning in circles (rotating) and the like. In certain optional embodiments, the top camera 1502 is also used to determine which of the side-view cameras 1605 to use to view the animal in profile. In the illustrated embodiment, the two side-view cameras 1605 are positioned at 90 degrees to each other, and have unobstructed views of the experiment through the two clear sides of the system 1510. Collectively, the top and profile views can be used to determine most if not all of the fine and gross bodily movements and positions of the animal.

In certain preferred embodiments, the image capture devices are compatible with standard NTSC or PAL video. In certain preferred embodiments, video capture occurs at a rate of at least 30 frames/second, in order to see fast activity of the animal such as startle response or twitching. In certain embodiments, the subject system utilizes high-resolution color video cameras which capture simultaneous, full-rate video. All three cameras can be connected to a computer, such as through a video digitizer or digital interface, in order to provide full frame-rate images from all three cameras to image processing software. In the illustrated embodiment, the leads from the cameras and, optionally, image processing software or buffer memory, can be gathered in the base 1508, that can be hinged 1604 for easy access into the base compartment.

The illustrated embodiment shows a lighting source 1601, though ambient light can be used as well. In certain preferred embodiments, the lighting source 1601 uses LED or other flicker-free lighting (such as high frequency fluorescent lights), and preferably uses lighting that has instant on-off response and low heating ratings. In one embodiment, this board contains several hundred LEDs which may be of various and/or mixed colors. The LED lighting system can be connected to a controlling computer that can turn the lighting on and off to simulate nighttime and daytime conditions in the laboratory. LED lighting systems have a number of advantages over alternatives such as fluorescent and incandescent lights such as more compact size, cooler operation, better control of light color, and faster response time.

To measure eating and drinking behaviors, the illustrated system includes two water bottles 1507 and a feeding bin 1506. Such bottles and bins can be connected to touch sensor circuits, e.g., mechanical or electrical, which senses contact by the animal. The output of the touch sensor(s) can be connected to the computer and can be read by software to detect eating and drinking behaviors. These behaviors can be processed and recorded along with behaviors recognized by the computer vision system.

In the illustrated embodiment, the floor 1504 can be a slide-out bedding tray. Below the bedding tray, the exemplary system includes floor sensors 1505 which may include pressure or other force sensors or other means for measuring the weight of the animal. In certain embodiments, the subject system can be used for testing pre-pulse inhibition of startle (PPI). The PPI test is used in laboratories to evaluate an animal's ability to filter environmental stimuli. A key part of the test is measuring the startle response of the animal-essentially, how much force the animal exerts in a jump, in response to a loud noise or puff of air. A brief softer sound preceding the startling stimulus normally leads to an inhibition of the startle response. Measurement of the normal startle response and of the response after a prepulse can be made using a force sensing cage floor. The PPI measure is the percent inhibition produced by the prepulse. The force sensor floor is connected to the computer and continuously monitored by software to record startle events. This recorded data becomes part of the behavioral record and can be analyzed to measure the response amplitude and timing of the startle, and the PPI of the animal.

The floor can also include conductive leads for measuring cardiac impulses, e.g. EKG measurements.

In certain embodiments, the floor consists of many small, closely spaced square or round towers. These towers are tall enough and so closely spaced that the mouse must remain on top of the towers and can only move by stepping from one tower to the next. The tower floor is used for the high tower walk test experiment that measures misstepping between towers and provides high sensitivity to the sedative and ataxic effects of some drugs.

The system can also include camera screens 1603 that can be used to block out scenery outside the cage, and to provide a uniform colored background against which the animal is imaged.

In certain embodiments, the system 1510 includes instrument insert openings 1502 for positioning other instruments and probes in the cage 1602. Merely to illustrate, the sensors can include temperature sensors, nose poke sensors, a scale to measure mouse body weight, an ultrasonic microphone, telemetric sensors, and the like. Indeed, almost any commonly used laboratory sensor can be added to the subject system and integrated into a computerized data capture system. It is also contemplated that the subject system can include one or more additional actuators, such as automatic food or reward dispensers, lights and displays, speakers or other noise makers, enrichment devices (such as an instrumented running wheel), and the like.

To further illustrate, the subject system can include an air puff system. To induce a startle response, compressed air nozzles can be installed in the enclosure, e.g., through instrument insert openings 1502. These nozzles produce an abrupt, intense and (preferably) evenly distributed puff of air which causes the mouse to startle. The compressed air can be supplied by an external compressor and controlled by an electronic air valve. A standard pressure regulator allows adjustment of the air pressure going to the valve and nozzles. A computer interface allows the valve to be rapidly cycled under software control.

The subject system can also include a shocking probe. A preferred shocking probe can be a small, non-conductive cylinder spirally wrapped with a pair of conductive wires. The two wires run adjacent to each other but are never in contact. The close proximity of the wires makes it likely that any contact with the probe will touch both wires which are electrified with a high voltage. The voltage is current-limited by the power supply to restrict the shock to a harmless, but annoying level. The shocking probe is used in the defensive burying test which provides sensitivity to the anxiolytic and antidepressant effects of some drugs.

Example 4

Computer Control System

Figure 14:
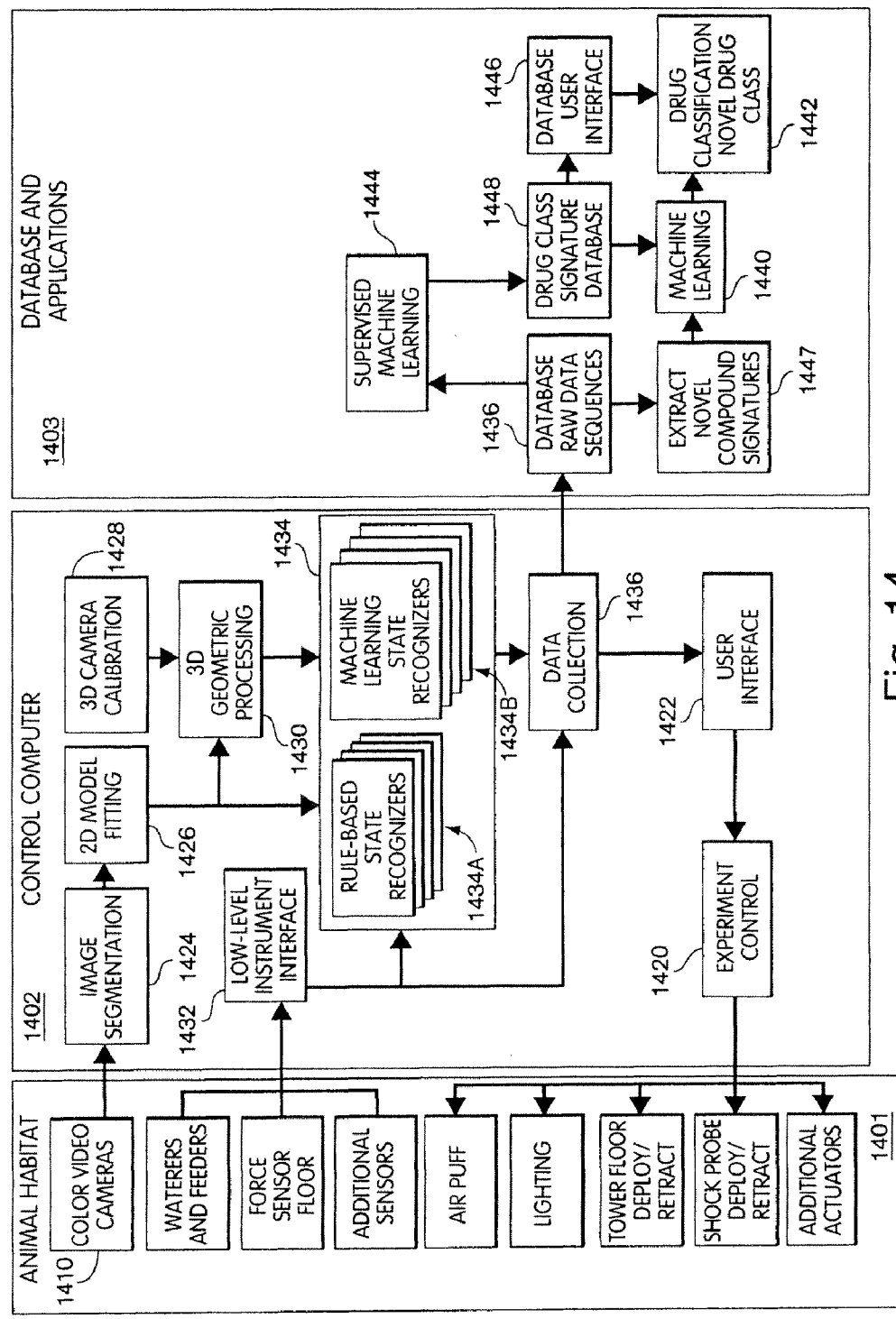

FIG. 14 shows a schematic representation of an embodiment of the subject system. In the example, the control computer system 1402 includes a User Interface module 1422. Operation of the habitat 1401 can be directed at least in part from, e.g., a graphical user interface that allows control over habitat operation. The User interface 1422 can provide windows through which the operator can observe sensor readings, control lighting, and trigger other events. Additionally, the User Interface 1422 permits the operator to load and predefine sequences of commands for execution by the Experiment Control Module 1420. For example, a predefined sequence might call for 30 minutes of observation under bright lighting, followed by deployment of the Shock Probe for 10 minutes, and ending with an Air Puff and 5 minutes of reduced lighting. Using these predefined sequences, many different mice can be exposed to nearly identical test conditions in one or more habitats, run sequentially or in parallel, respectively.

As indicated, the exemplary animal habitat 1401 includes cameras 1410 for capturing images of the observed animals, the output from the cameras being processed by a control computer system 1402. The computer system 1402 can include an Experiment Control module 1420. In many embodiments, it is contemplated that digital and analog I/O hardware is used to interact with the habitat's actuators and sensors. The Experiment Control module 1420 can use this I/O hardware to convert commands from the User Interface module 1422 into electrical signals, which actuate the habitat's hardware. The Experiment Control module 1420 can also include simple timing and scheduling software for executing predefined sequences of commands and standard experiments.

The illustrated system also includes an Image Segmentation module 1424. This module can be a software or hardware component and takes a video image and labels pixels as animal or non-animal (background). An exemplary implementation uses a combination of techniques including frame-to-frame differencing, background subtraction, color segmentation, and connected components analysis to discriminate between those pixels which make up the animal and those which make up the background and bedding.

The data from the Image Segmentation module 1424 can then be subjected to 2D Model Fitting 1426. For example, segmented images can be processed by fitting a set of 2D models to the labeled regions. In addition to traditional geometric primitives, such as bounding box, center of mass, and best-fit-ellipse, more specific geometric models, tailored to the specific shape of the animal can be used. These 2D models include elements corresponding to specific anatomical features, such as the nose, shoulders, rump, and base of the tail.

In one implementation, knowledge of the relative positions and orientations of the three cameras is used to guide the 2D model fitting. The location of the animal in a particular camera view is related to its location in each of the other views, and this information is used to constrain the 2D model fitting process.

The illustrated system also includes a module for Camera Calibration 1428. The 3D positions, orientations, and imaging characteristics of the habitat's cameras are recovered through a 3D calibration procedure. For example, an calibration target which is marked with a collection of highly visible and accurately placed dots can be placed inside the habitat. Simultaneous images are acquired from all three cameras, and the dots are located in each image. A nonlinear optimization routine can be used to recover the characteristic distortions and projection parameters of each camera, as well as the position and orientation of each camera with respect to the calibration target. These data, taken collectively, also define the positions of the three cameras with respect to each other.

Referring again to the system of FIG. 14, the positions of features in the 2D geometric models, along with the 3D camera calibration 1428, are used to compute 1430 the approximate 3D locations and velocities of parts of the mouse, such as the center of the mouse, the mouse's shoulders, and the mouse's rump. The trajectories and relative positions of these 3D anatomical features can be tracked over time and recorded for use in behavior identification.

Collectively, data from the 2D Model Fitting 1426 and 3D Geometric Processing 1430 modules is referred to, for this example, as the "computer vision modules".

In certain embodiments, the control computer system 1402 can also include a Low-Level Instrument Interface 1432. As indicated in the figure and herein, in addition to the image capture systems, the habitat can also includes a variety other sensors for monitoring animal activity. Readings and observations from each of these sensors is preferably synchronized with the video observations and logged. The Low-Level Instrument Interface 1432 can be set up to buffer the input from these types of data acquisition hardware and apply any necessary pre-processing steps, such as low-pass filtering to reduce signal noise. Each processed sensor reading is preferably time stamped and passed to the Data Collection module 1436.

The illustrated system also includes a Classifier Module 1434. That module may be used to annotate data obtained from the habitat 1401. The Classifier Module 1434 may include one or more Rule-Based State Recognizers 1434A. In certain embodiments, animal activity can be described using a collection of accepted states, such as rearing, digging, climbing, scratching, etc. State labels are assigned to segments of video by passing the output of both 2D and 3D processing algorithms through a set of decision rules. States such as locomotion and immobility can be identified by averaging the velocity of the center of the animal over a short time period, and then comparing these average values with empirically chosen thresholds. Other states are identified using rules conditioned on the positions and velocities of 3D anatomical features, the positions of 2D anatomical features, and image pixel values. Yet other states may be identified with the help of 1434B Machine Learning State Recognizers, as described below.

The Classifier Module 1434 may also include one or more Machine Learning State Recognizers 1434B that comprise supervised and unsupervised learning algorithms. Supervised Machine Learning State Recognizers 1434B can be used to capture some pre-determined states that may be difficult to recognize using Rule-Based State Recognizers 1434A such as subtle or complex movements.

The set of recognized states need not be limited to those explicitly defined in the Rule Based State Recognizers 1434A. Additional patterns of animal activity and sensor readings can be detected by the Unsupervised Machine Learning State Recognizers 1434B. These software components monitor the data stream and search for general patterns of behavior such as sequences of states (e.g., rearing follow by grooming follow by jumping), or combinations of data input from the Sensors (e.g. grooming with high heart rate) that occur with such high frequency that are assumed to carry information.

The illustrated Control Computer system 1402 also includes a Data Collection module 1436. Data from the Computer Vision modules and Low Level Instrument interface 1432 can be passed to the Data Collection module 1436, which can serve as a management system for system data. Other modules which require sensor readings or computer vision output can also connect to the Data Collection Module 1436, which synchronizes the data from its various inputs, and acts as a storage Raw Data and Sequence Database 1436, by storing experimental data from each individual subject for further processing.

The data corresponding to reference compounds stored in the Raw Data and Sequence Database 1438 can be queried by a Supervised Machine Learning module 1444. Supervised learning techniques, such as Bayes Classifiers, Support Vector Machines, and Mixture models can be used to extract those characteristics of the experimental data that permits successful classification into pre-determined therapeutic classes (e.g. antidepressants). The summarized data for each drug, the drug signature, is stored in the Drug Class Signature Database 1448. The data corresponding to a test or novel compound stored in the Raw Data and Sequence Database 1436 can be queried by a Module 1447 that extracts the appropriate summary data or novel or test drug signature. Such signature is compared against the reference Drug Class Signature Database 1448, by a Machine Learning module 1440, which may used diverse learning algorithms, and which classifies the novel or test drug signature into the existing drug classes previously defined by the Supervised Machine Learning module 1444.

The Drug Class Signature Database 1448 and the classification output module 1442 communicate with one or more Servers 1446: A server interface can be used to provide access to the Behavioral Database 1438 for local and remote access to the data. The server can support direct queries of the database, and provide interfaces for additional machine learning algorithms, database search algorithms, and tools for correlating query data with entries in the database.

Furthermore, since numerous modifications and variations will readily occur to those skilled in the art, it is not desired that the present invention be limited to the exact construction and operation illustrated and described. Accordingly, all suitable modifications and equivalents, which may be resorted to, are intended to fall within the scope of the claims.

It is to be further understood that while alternate embodiments may not have been presented for every portion or component of the invention, and that the instant invention can compose many different combinations of described portions, or that other undescribed alternate embodiments may be available or substituted for a described portion, such is not to be considered a disclaimer of those alternate embodiments. It will be appreciated that many of those undescribed embodiments are within the literal scope of the following claims, and others are equivalent. Again, it is recognized that the order or sequence of tasks illustrated in these examples and the attached figures are merely intended to be exemplary of the concepts defined herein.

We claim:

1. A method of predicting whether a test treatment belongs to a class of test treatments having a pattern of animal behavior associated with said class of test treatments, said method comprising:
   (a) administering a test treatment to at least one animal;
   (b) using a computer to capture behavioral data of said at least one animal administered said test treatment;
   (c) using a computer to compare information derived from an analysis of the captured data from (b) with stored class signature information from a database comprising signatures associated with treatment classes to predict a probability that the test treatment is a member of at least one treatment class represented in the stored class signature information, wherein said stored signature information was obtained by:
       (i) collecting behavioral data from animals administered at least one known treatment which is a member of a class of treatments; and (ii) using a computer to define said signatures for said treatment class by correlating features of said behavioral data with said known treatment class member; and (iii) storing said signature information in a computer; and
   (d) outputting a result from (c) that is indicative of whether said test treatment is a member of at least one treatment class.

2. The method of claim 1 wherein the captured data comprises information from one or more video cameras.

3. The method of claim 1 wherein the captured data comprises information from one or more video cameras and generates three-dimensional positions, orientations, and/or imaging characteristics of said at least one animal.

* * * * *